(12) United States Patent
Orr et al.

(10) Patent No.: US 6,824,520 B2
(45) Date of Patent: Nov. 30, 2004

(54) METHOD AND APPARATUS FOR TRACKING USAGE OF A RESPIRATORY MEASUREMENT DEVICE

(75) Inventors: Joseph Orr, Park City, UT (US); Scott Allen Kofoed, Bountiful, UT (US)

(73) Assignee: Pulmonary Data Services, Inc., Louisville, CO (US)

( * ) Notice: Subject to any disclaimer, the term of this patent is extended or adjusted under 35 U.S.C. 154(b) by 0 days.

(21) Appl. No.: 10/251,286

(22) Filed: Sep. 20, 2002

(65) Prior Publication Data

US 2003/0116159 A1 Jun. 26, 2003

Related U.S. Application Data

(60) Provisional application No. 60/324,207, filed on Sep. 21, 2001.

(51) Int. Cl.[7] .................................................. A61B 5/08
(52) U.S. Cl. ...................................... 600/529; 600/532
(58) Field of Search .............................. 600/529, 531, 600/532, 533, 538, 537; 128/204.23

(56) References Cited

U.S. PATENT DOCUMENTS

| | | | |
|---|---|---|---|
| 3,659,589 A | 5/1972 | Lambert | |
| 4,897,789 A | 1/1990 | King et al. | |
| 5,303,575 A | * 4/1994 | Brown et al. ................. | 73/23.3 |
| 5,337,793 A | 8/1994 | Gold et al. | |
| 5,357,972 A | 10/1994 | Norlien | |
| 5,390,668 A | 2/1995 | Lehman | |
| 5,400,267 A | 3/1995 | Denen et al. | |
| 5,425,375 A | 6/1995 | Chin et al. | |
| 5,564,432 A | 10/1996 | Thomson | |
| 5,715,831 A | 2/1998 | Johnson | |
| 5,722,417 A | 3/1998 | Garbe | |
| 5,735,287 A | 4/1998 | Thomson | |
| 5,924,994 A | 7/1999 | Harbrecht et al. | 600/532 |
| 5,980,466 A | 11/1999 | Thomson | 600/538 |
| 5,989,917 A | 11/1999 | McAleer et al. | |
| 5,997,483 A | 12/1999 | Johnson | 600/538 |
| 6,017,354 A | 1/2000 | Culp et al. | |
| 6,019,731 A | 2/2000 | Harbrecht et al. | 600/532 |
| 6,036,458 A | 3/2000 | Cole et al. | |
| 6,042,551 A | 3/2000 | Harbrecht et al. | 600/532 |
| 6,113,549 A | 9/2000 | Johnson | 600/529 |
| 6,190,326 B1 | 2/2001 | McKinnon et al. | 600/529 |
| 6,238,353 B1 | 5/2001 | Weinstein et al. | 600/540 |
| 6,332,867 B1 | * 12/2001 | Chen et al. | 600/300 |
| 6,447,459 B1 | 9/2002 | Larom | |
| 6,656,127 B1 | * 12/2003 | Ben-Oren et al. | 600/532 |

OTHER PUBLICATIONS

Pulmonary Data Service, Inc. Brochure, (undated), 20pages.

* cited by examiner

Primary Examiner—Robert L Nasser
Assistant Examiner—Navin Natnithithadha
(74) Attorney, Agent, or Firm—Sheridan Ross P.C.

(57) ABSTRACT

The present invention is directed to a reusable respiratory measurement device having a discardable flow tube in which a counter is included in a detachable (discardable) memory unit that removably engages the respiratory measurement device body. The memory unit includes a counter that tracks usage of the respiratory measurement device and disables the respiratory measurement device when usage has reached certain predetermined thresholds. The memory unit is then replaced with a new memory unit which re-enables the respiratory measurement device for further measurements. The memory unit is typically sold as part of a batch or lot of disposable flow tubes in which case the counter value is commonly the same as the number of flow tubes in the batch or lot.

69 Claims, 15 Drawing Sheets

METHOD AND APPARATUS FOR TRACKING USAGE OF A RESPIRATORY MEASUREMENT DEVICE

CROSS REFERENCE TO RELATED APPLICATION

Priority is claimed from U.S. Provisional Patent Application No. 60/324,207 filed Sep. 21, 2001, entitled "METHOD AND APPARATUS FOR TRACKING USAGE OF A RESPIRATORY MEASUREMENT DEVICE," which is incorporated by reference in its entirety.

FIELD OF THE INVENTION

The present invention is directed generally to reusable respiratory measurement devices which employ disposable components, and specifically to reusable spirometers having disposable flow tubes.

BACKGROUND OF THE INVENTION

Respiratory measurement devices are commonly used to monitor lung performance of patients having respiratory ailments. In such applications, lung performance parameters, such as peak air flow, are periodically taken and recorded manually or electronically in a diary. If lung performance falls below a certain level or if the diary shows a deterioration in lung performance, the patient seeks medical assistance.

Such lung performance is commonly monitored using spirometry. Spirometry, the evaluation of lung function with a spirometer, is one of the simplest, most common pulmonary function tests and may be necessary for any/all of the following reasons: to determine how well the lungs receive, hold, and utilize air; to monitor a lung disease; to monitor the effectiveness of treatment; to determine the severity of a lung disease; and to determine whether the lung disease is restrictive (decreased airflow) or obstructive (disruption of airflow). As will be appreciated, a spirometer is an instrument for measuring the volume or air entering or leaving the lungs. When conducting a measurement, after taking a deep breath, a patient forcefully breathes out into the spirometer as completely and forcefully as possible. The spirometer measures and records both the amount of air expelled and how quickly the air was expelled from the lungs.

In the case of a patient who closely monitors their lung performance, it is useful to have a respiratory measurement device which is not only inexpensive and portable, but also accurate. Many inexpensive respiratory measurement devices have components which are designed to be used only once or a limited number of times. If the component is used beyond its useful life, erroneous readings may result. The erroneous readings may be the result of condensation building up within the component. This may also be due to the component being made of a relatively low-cost material which is likely to break down after a number of uses. For example, a spirometer may have a disposable component, such as a pneumotach, which typically has a fixed or variable orifice and a pressure transducer located on one or both sides of the orifice, pneumotach is a component which typically contains a pressure sensing transducer capable of measuring the amount of force exerted by the lungs in respiration. A fixed orifice is a reduced diameter passage, which can have any shape, having a fixed cross-sectional area that is independent of air flow rate. A variable orifice is a reduced diameter passage, which can have any shape, having a cross-sectional area that is dependent on air flow rate (e.g., the cross-sectional area increases as the flow rate increases). In either case, the orifice in the pneumotach may become deformed after use, resulting in erroneous measurements if the pneumotach is reused. An inaccurate measurement can cause patient misdiagnosis and/or dissatisfaction, particularly if a determination to obtain medical assistance is based on such an inaccurate measurement.

In such devices, it is necessary to replace any components which are likely to produce inaccurate readings prior to the component having significant change in condition which may reduce the accuracy of a measurement. Although directions of use can specify a components useful life, many patients often fail to read such directions and/or often reuse such components well after their useful lives, which may result in inaccurate measurements.

Additionally, such devices are often used in clinical settings, such as a hospital, clinic, or doctor's office. In such situations, it is common for several patients to use a single portable respiratory measurement device. It is important that the mouthpiece for the device is either properly cleaned, or replaced. To provide customer convenience, portable respiratory devices commonly have disposable mouthpieces, which are replaced prior to a new patient using the device. The disposable mouthpiece helps to reduce the chances of any cross-contamination between patients using the same portable respiratory device and/or the detrimental health effects of bacteria and other microbes on the mouthpiece.

Furthermore, when disposable components are manufactured, they often have properties which are somewhat different depending upon several factors present in the manufacturing process. Thus, it is also important to have correct calibration information for such components. For example, a disposable pneumotach manufactured in a first manufacturing lot may have a slightly different orifice than a disposable pneumotach manufactured in a second manufacturing lot. Furthermore, within the same manufacturing lot, two disposable pneumotachs may have a different orifice size. These different orifice sizes must be correctly accounted for in the spirometer to ensure an accurate respiratory measurement from the spirometer. Likewise, it is important that calibration information for any such disposable component be used when determining a reading from such a device.

SUMMARY OF THE INVENTION

The present invention provides a methodology for tracking usage of disposable components, including pneumotachs or air tubes, in respiratory measurement device applications. While described with respect to respiratory applications, the invention can also be used in other applications which use non-respiratory devices that measure or detect airflow or a parameter associated therewith. A memory counter is employed to determine whether or not component usage has equaled predetermined limits and, if so, disables the respiratory measurement device. A counter is a functional unit with a number of states, each of which is associated with an incident of one or more selected events. The counter can be altered upon an appropriate signal associated with an incident of the selected event. The device can be thereafter enabled by any suitable technique, such as by replacing an old disposable memory with a new disposable memory to re-enable the respiratory measurement device, or by removing and/or attaching a selected component. In one variation, a disposable memory includes not only the counter but also calibration information.

The present invention, in its differing embodiments and configurations, can ensure that the air tubes (or devices that transport or channel airflow) are not re-used among different patients thereby reducing or eliminating cross-contamination among patients, and/or increasing the accuracy of the spirometer readings by reducing condensation buildup within the disposable air tubes and providing unique calibration information associated with a lot or batch of air tubes which can take into account performance variations among batches or lots of air tubes.

In one embodiment of the present invention, a respiratory measurement device for measuring a pulmonary condition of a patient includes:
  (a) a processor operable to determine at least a first respiratory parameter based on at least a first measurement signal;
  (b) a memory operable to store calibration information to determine the first respiratory parameter and a counter for tracking a number of respiratory measurements; and
  (c) at least a first detachable component operable to receive a respiratory airflow of a user.

The processor and memory may be contained in a body member. The body member may be reusable. The memory can be any suitable information storage medium. For example, the memory can be one or more of ROM, PROM, EPROM, flash memory, non-volatile RAM, battery-backed-up RAM, EEPROM, a magnetic disk, and an optical disk. In one configuration, the memory module is contained in a unit that is detachable from the body member. The processor, and typically another memory module, are contained in the body member.

The first detachable component can be any suitable device for transporting or conducting a gas flow and/or measuring a parameter associated with a gas flow. By way of example, the first detachable component can be a flow tube, a pneumotach, an air tube, a respiratory filter, or mouthpiece. The first detachable component is typically an air tube. The air tube can include a sensor to provide the first measurement signal. The detachable component can measure any desirable respiratory parameter. For example, the respiratory parameter can be one or more of PEF, FEV1, FEV6, FEV1/FEV6, FVC, FEV1/FVC, and FEF25-75. In one configuration, the detachable component is disposable. Examples of detachable components include those disclosed in U.S. Pat. Nos. 5,997,483; 6,042,551; 5,564,432; 3,659,589; 5,722,417; and 5,357,972, each of which is incorporated herein by this reference.

In another embodiment, a method for monitoring use of a respiratory measurement device is provided that includes the steps of:
  (a) engaging a flow tube with the respiratory measurement device;
  (b) optionally engaging a monitoring unit with the respiratory measurement device, the monitoring unit including a memory including calibration information associated with at least one of the respiratory measurement device and the flow tube and a counter for determining a number of measurements taken by the respiratory measurement device;
  (c) performing a respiratory measurement with the respiratory measurement device; and
  (d) decrementing or incrementing the counter in response to the performing step.

The last step can be performed in a number of different ways and can be performed at a number of different times. By way of example, the counter value, in one configuration, is initially set to a permitted number of tests and is decremented by one for each test or measurement. In this configuration, the respiratory measurement device has a processor which typically determines after each test if the counter is equal to zero and, if so, disables the respiratory measurement device. In another configuration, the counter value is initially set to zero and is incremented by one for each test or measurement. In this configuration, the processor compares after each test the incremented counter to a permissible number of tests stored in the respiratory measurement device memory or in the memory of the enabling device or monitoring unit and if the permissible number of tests has the same value as the counter disables the respiratory measurement device. Step (d) can be performed after a new air tube is attached to the respiratory measurement device, when a used air tube is removed from the respiratory measurement device, immediately before, during, or after a measurement is taken, etc.

The method can include additional steps. For example, the method can further include, the steps of:
  removing the monitoring unit from the respiratory measurement device;
  engaging a second monitoring unit with the respiratory measurement device; and
  enabling the respiratory measurement device in response to the prior step.

The last step can include the steps of reading both a second memory and a second counter in the second monitoring unit.

In another embodiment, a method for supplying a disposable flow tube for a respiratory measurement device is provided that includes the steps of:
  (a) manufacturing a first plurality of disposable flow tubes for a respiratory measurement device;
  (b) determining first calibration information for the first plurality of flow tubes;
  (c) manufacturing a first enabling device, including a first memory storing at least one of the first calibration information and a first counter for counting a number of measurements performed by the respiratory measurement device; and
  (d) packaging the first plurality of disposable flow tubes together with the corresponding first enabling device for use by a respiratory measurement device user.

Typically, the first counter is set to the number of the first plurality or batch of flow tubes. The calibration information is determined for the entire batch of flow tubes by any suitable technique. The calibration information can be based on the median performance characteristics for the batch, the average or mean performance characteristics for the batch, dimensional measurements for the batch, signal strength for one or more flow rates for the batch, or hardware used to manufacture the batch of flow tubes.

The method is typically performed on a batch-by-batch basis. For example, the method can include the further steps of:
  (e) manufacturing a second plurality of disposable flow tubes;
  (f) determining second calibration information for the second plurality of flow tubes;
  (g) manufacturing a second enabling device, including a second memory storing the second calibration information and a second counter for counting a number of measurements performed by a respiratory measurement device attached to one of the second plurality of flow tubes; and
  (h) packaging the second plurality of disposable flow tubes together with the corresponding second enabling device for use by a respiratory measurement device user.

In one configuration, the second plurality of flow tubes and second enabling device are in a different package than the first plurality of flow tubes and first enabling device. In one configuration, the first calibration information differs from the second calibration information. In one configuration, the first counter has the same value as the second counter. As will be appreciated, the flow tubes can be sold in different batch sizes so that in other configurations the first and second counters will have differing values.

The above summary is neither complete nor exhaustive. As will be appreciated, the various features noted above can be combined or separated in a variety of other embodiments and/or configurations, depending on the application. Such other embodiments and/or configurations are considered to be a part of the present invention.

DETAILED DESCRIPTION

Figure 1:
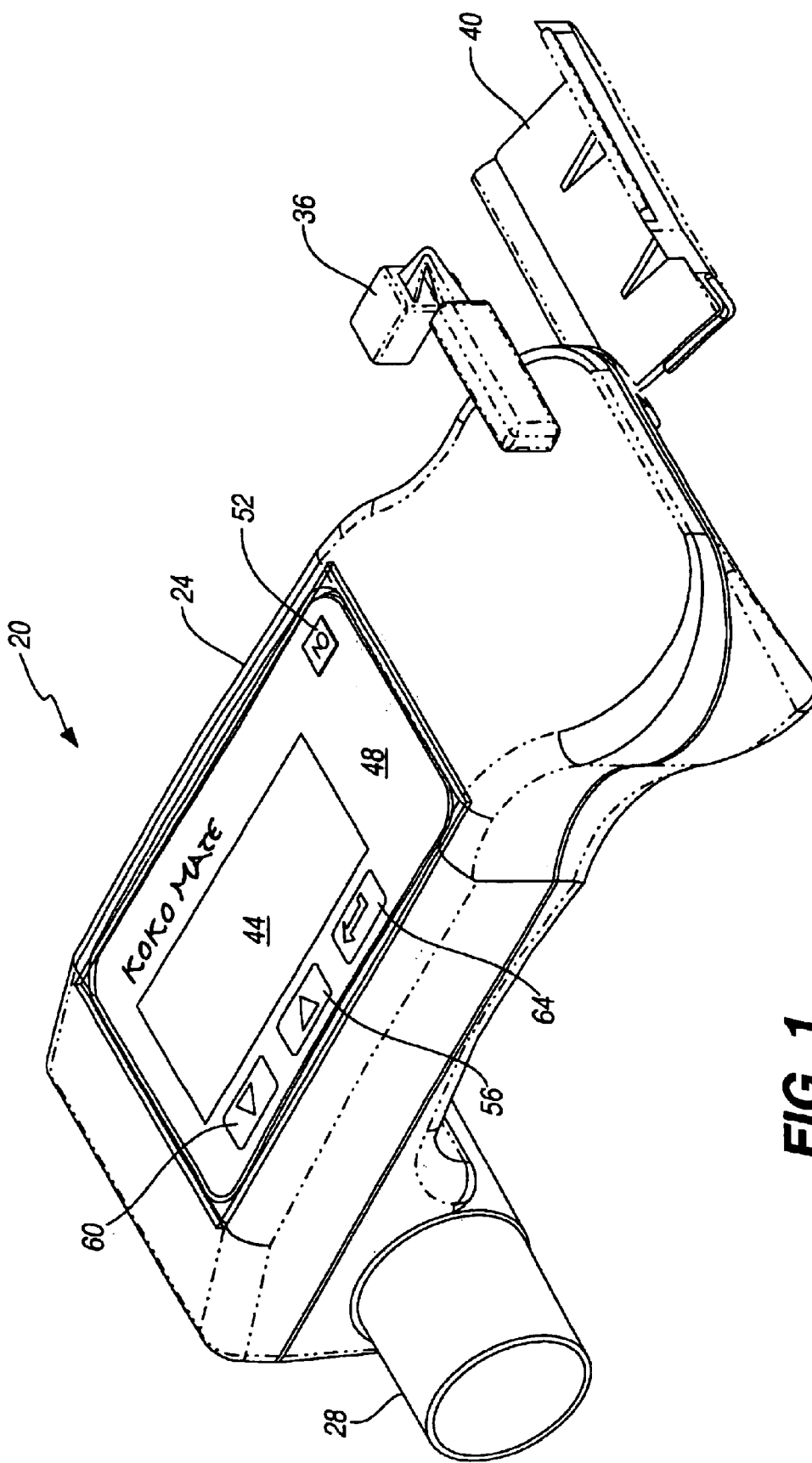
FIG. 1 is a front perspective view illustrating one embodiment of the present invention.
Figure 2:
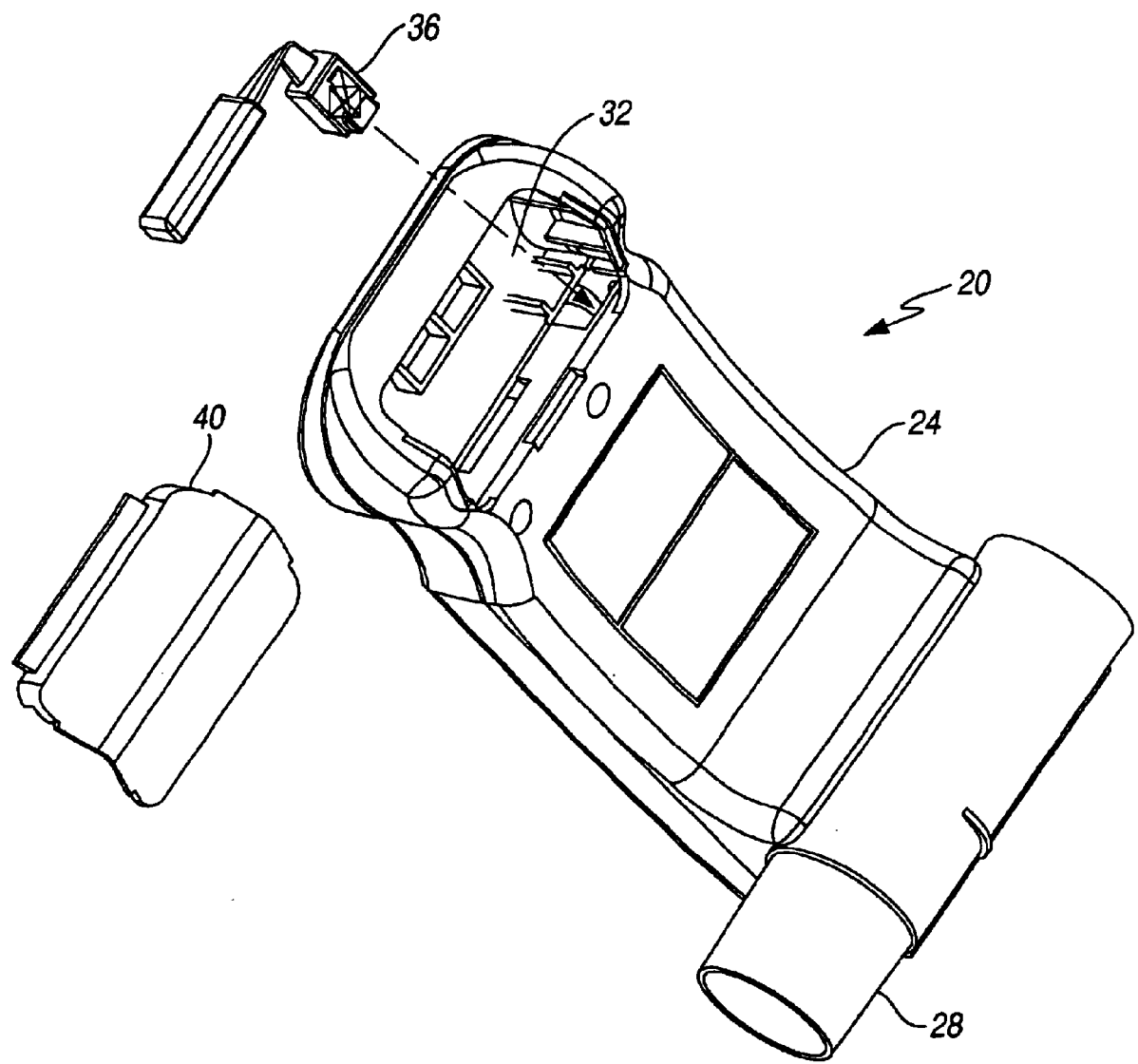
FIG. 2 is a back perspective view illustrating one embodiment of the present invention.
Figure 3:
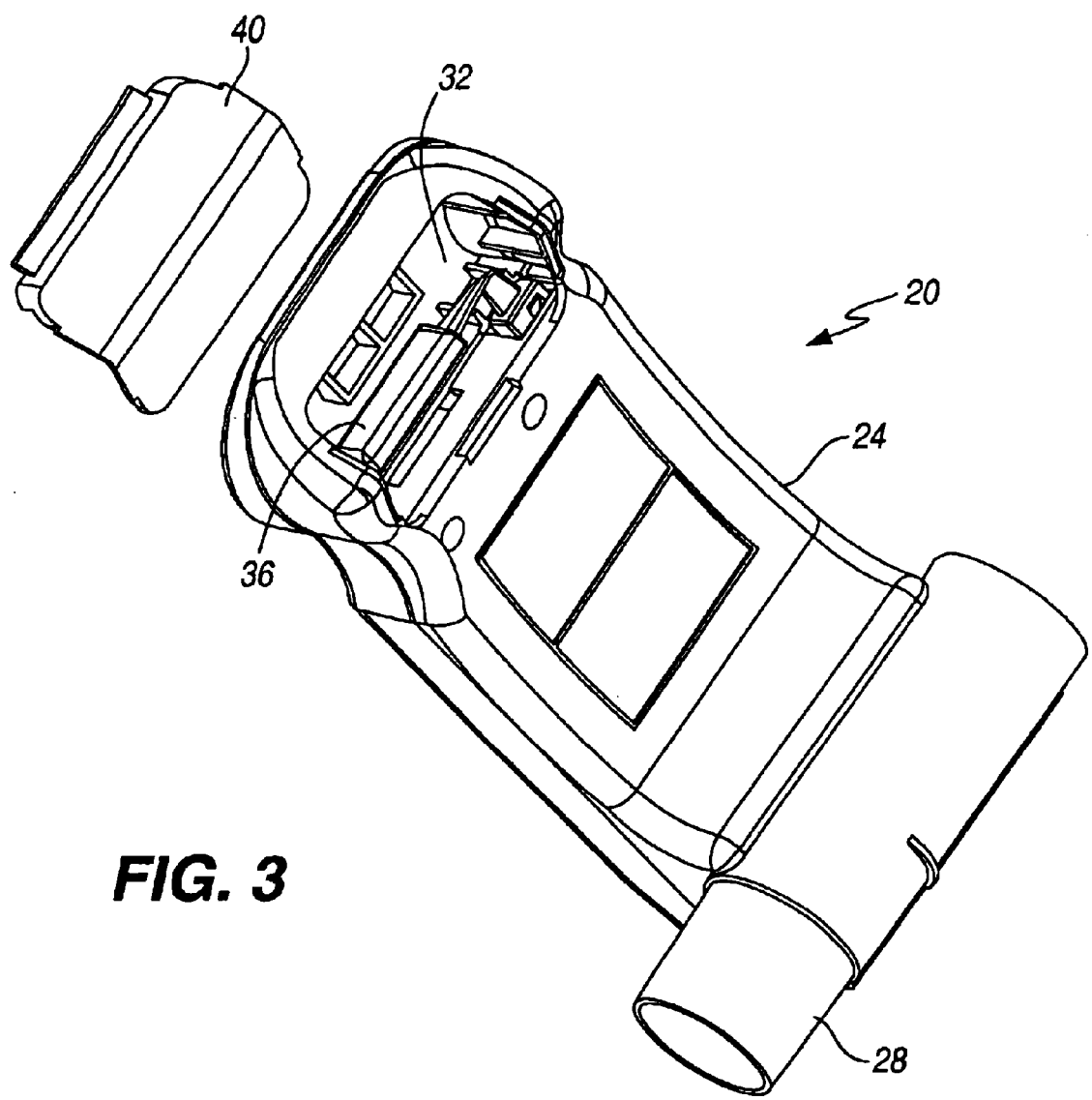
FIG. 3 is a back perspective view illustrating one embodiment of the present invention.

Referring to FIGS. 1 and 2, one embodiment of the respiratory measurement device of present invention is illustrated. The respiratory measurement device 20 is a spirometer which includes a body portion 24, and a disposable flow tube 28. The body portion 24 has a cavity 32 which is able to receive a memory element (also referred to as a monitoring unit or device) 36. In the embodiment illustrated, the memory element 36 is inserted into the body member 24 through the cavity 32, which is a battery compartment of the body member 24, and is covered by a battery cover 40 which engages the body member 24 to cover the batteries (not shown) and the memory element 36. FIG. 3 illustrates the respiratory measurement device 20 with the battery cover 40 removed, and the memory element 36 fully inserted into the body member 24.

The body portion includes a display 44, and a keypad 48. In the embodiment shown, the keypad 52 includes four keys. The keys include a power key 52, an up arrow key 56, a down arrow key 60, and an enter key 64. In this embodiment, the display 44 is used to display a menu system, with the up/down arrow keys 56,60 used to highlight items from a menu, and the enter key 64 is used to select the menu item which is highlighted. The operation of the respiratory measurement device 20 will be described in further detail below. The body portion in another embodiment also includes a connector which can be connected to an external keyboard or computer. Furthermore, a data port may also be included, which may be connected to an external computer or other device and used to upload or download data between the respiratory measurement device and an external device.

In one embodiment, the flow tube 28 is a disposable component which is purchased by a user in a lot or batch. For example, a user may purchase a package having a plurality of disposable flow tubes 28. The flow tubes 28 are disposable, and are thus made primarily of an inexpensive material, which may deteriorate after use. Furthermore, if more than one user conducts respiratory measurements using the respiratory measurement device 20, the flow tube 28 is replaced, in order to reduce cross-contamination between users. Thus, the flow tubes 28 are required to be replaced periodically. Because different lots of flow tubes 28 may have different physical properties, calibration information related to the physical properties of the flow tubes 28 is required in order to ensure an accurate measurement of the respiratory parameter being measured by the respiratory measurement device 20. In one embodiment, each lot of flow tubes 28 has an associated memory element 36 which contains calibration information for the flow tubes 28. When all of the flow tubes 28 in the lot are used, the memory element 36 is removed and replaced with a memory element 36 associated with a second lot of flow tubes 28. Furthermore, in order to ensure that a second lot of flow tubes 28 is not used with the respiratory measurement device 20 without the memory element 36 being replaced, the memory element 36 may include information related to the number of tests performed by the respiratory measurement device 20, and disable the respiratory measurement device 20 when the number of flow tubes 28 present in the associated lot are consumed.

In one embodiment, a number of flow tubes 28 are manufactured. The physical characteristics of each flow tube 28 is then measured using a testing apparatus. Based upon the measured characteristics, the flow tubes 28 are sorted into bins, with each bin containing flow tubes 28 having similar physical properties. In one embodiment, there are ten bins, with flow tubes 28 with similar characteristics being sorted into the same bin. For example, one physical characteristic which may be measured is the orifice size in the flow tube 28. As a result of tolerances in the manufacturing process used to fabricate the flow tubes 28, the orifice size or flow calibration characteristics may vary between a minimum and a maximum, for example the orifice size may vary between 5 mm and 6 mm.

In this embodiment, this 1 mm tolerance is divided by ten, giving 0.1 mm bins, resulting in a bin for flow tubes with orifices between 5.0 and 5.1 mm, a bin for 5.11–5.2 mm, etc. It will be understood that these numbers are for discussion purposes only, and that the orifice size may be any appropriate size for the particular application, and the number of bins or the amount of tolerance will be selected such that any required calibration is valid for all components which are sorted into a bin. A number of flow tubes are packaged together, along with a memory element which contains calibration information for that particular bin. Then a respiratory measurement is taken using the flow tube, the respiratory measurement device reads the calibration factor from the memory element and a uses this information to determine the correct measurement to report to the user. The flow tubes can measure any desirable respiratory parameter. For example, the respiratory parameter can be one or more of PEF, FEV1, FEV6, FEV1/FEV6, FVC, FEV1/FVC, and FEF25–75.

Figure 4:
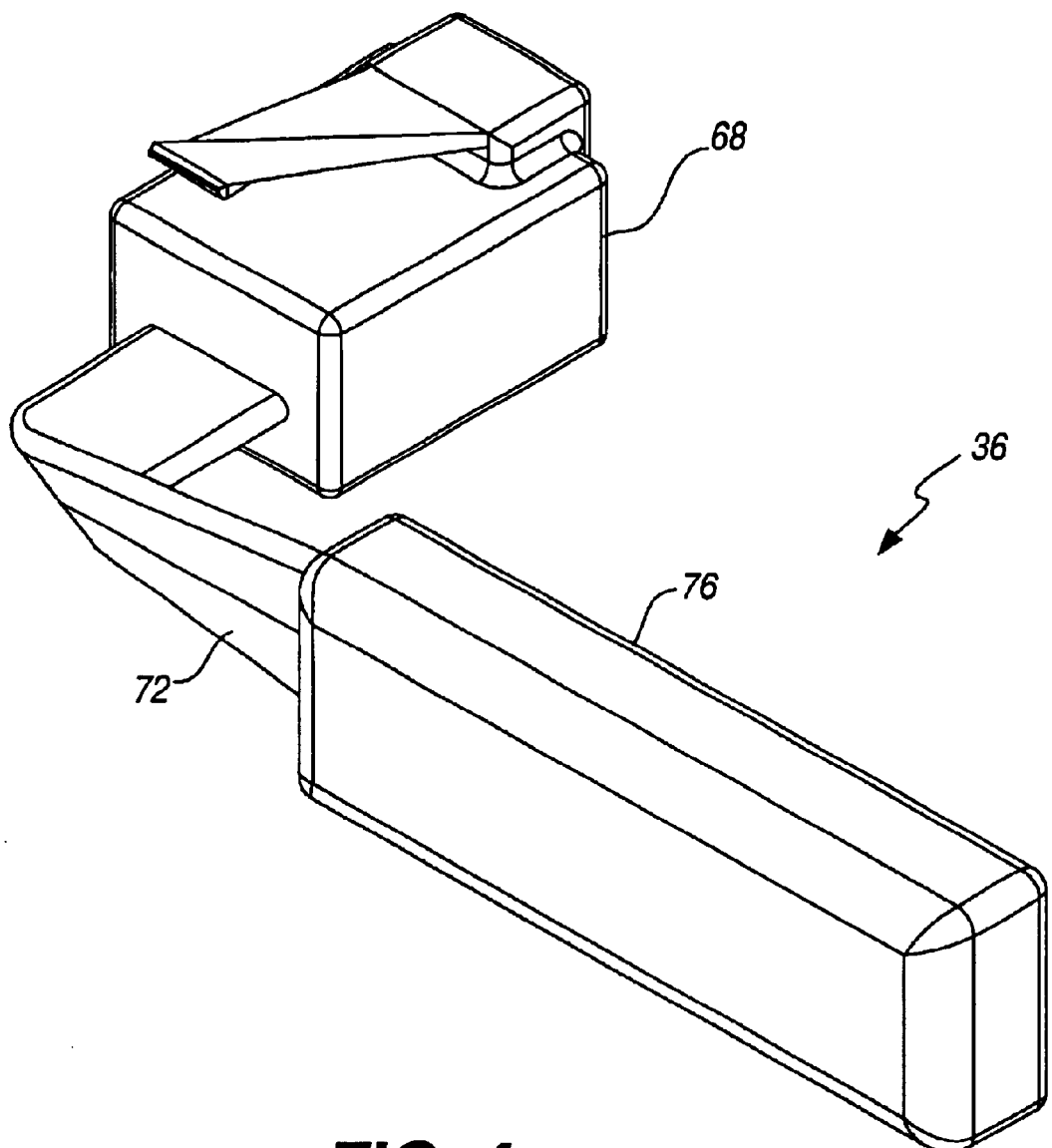
FIG. 4 is an illustration of the memory element of one embodiment of the present invention.

Referring now to FIG. 4, a memory element 36 of one embodiment is illustrated in greater detail. The memory element 36 has a connector 68, a cable 72, and an electronics portion 76. In one embodiment, the connector 68 is a four-pin RJ type connector, which engages with an appropriate receiving type connector within the body member 24. The cable 72 which electrically connects the electronics portion 76 with the connector 68 is a four-conductor ribbon-type cable. The electronics portion 76, in one embodiment, includes a printed circuit board (PCB) which connects to the cable 72, and has an electronically erasable programable read-only memory (EEPROM), commonly referred to as flash memory. The PCB in this embodiment is encased within a protective plastic cover. It will by understood that a number of different memory elements 36 can be employed in such a device, having a number of different connectors and different electronics. For example, the memory element 36 may have a battery powered SRAM, ROM, PROM, EPROM, non-volatile RAM, battery-backed-up RAM, or magnetic or optical media.

Figure 5:
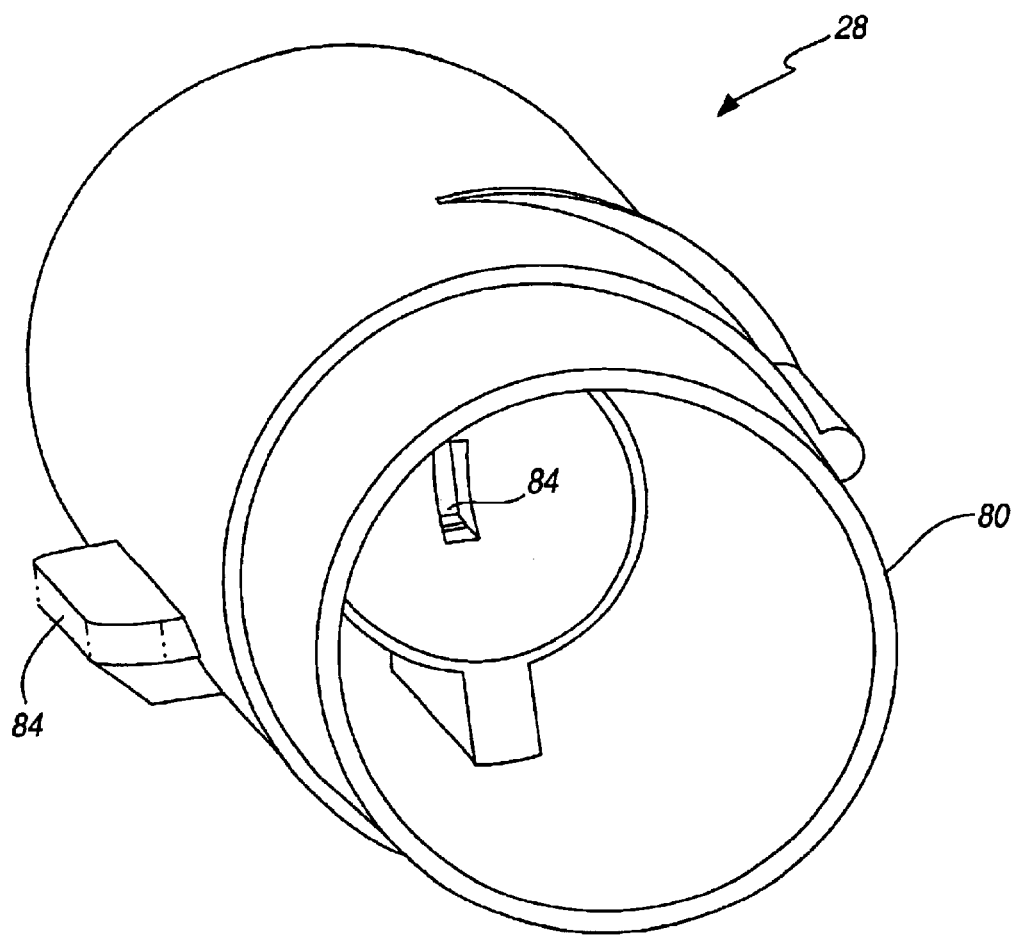
FIG. 5 is an illustration of a flow tube of one embodiment of the present invention.

Referring now to FIG. 5, a more detailed view of a disposable flow tube 28 of one embodiment is illustrated. The flow tube 28 is a pneumotach which includes a casing 80 having a pair of tabs 84. The pair of tabs 84 engage with the body member 24 when the flow tube 28 is inserted into the body member 24. Within the casing 80 is a fixed orifice 84. As mentioned above, the flow tube 28 is a disposable component, having certain physical characteristics. The size of the fixed orifice 84 is one such physical characteristic which, in order for the respiratory measurement device 20 to have an accurate measurement, must be calibrated. In one embodiment, the memory element 36 contains calibration information related to such physical characteristics.

Figure 6:
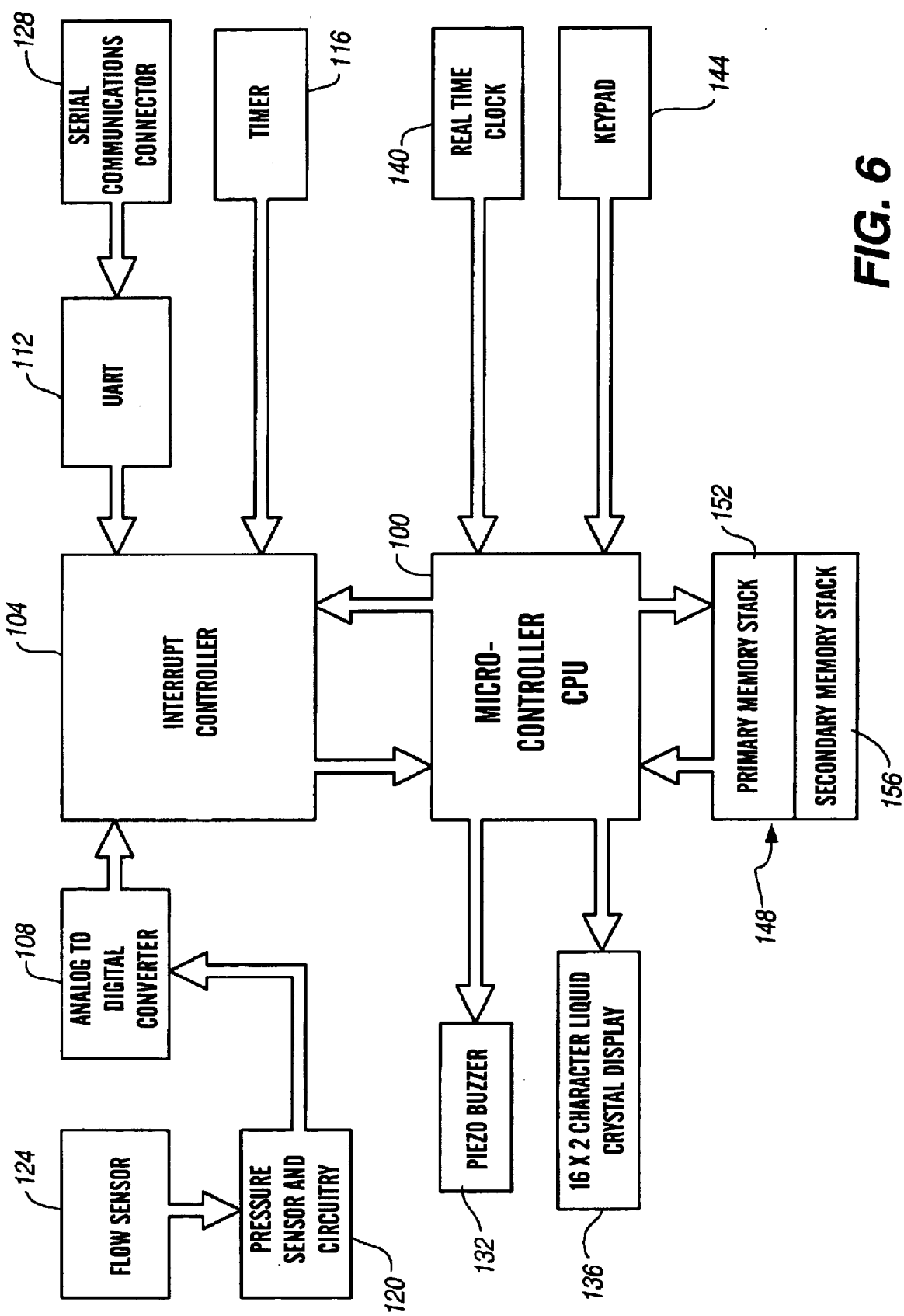
FIG. 6 is a block diagram illustrating the electronic components of one embodiment of the present invention.

Referring now to FIG. 6, a block diagram schematic of the electronics of the respiratory measurement device 20. A microcontroller CPU 100 is connected to a number of components. An interrupt controller 104, which receives signals from an analog to digital converter 108, a Universal Asynchronous Receiver/Transmitter (UART) 112, and a timer 116. The analog to digital converter 108 converts an analog signal received from pressure sensor circuitry 120 into a digital signal for delivery to the microcontroller CPU 100. A flow sensor 124 is connected to the pressure sensor and circuitry 120, which outputs an electronic signal which is proportional to the amount of air flow through the flow sensor 124. In one embodiment, the flow sensor 124 is a pressure transducer. The UART 112 provides an interface between the interrupt controller 104 and a serial communications connector 128 which receives serial communications. The timer 116 provides timing information for the respiratory measurements that are taken.

The microcontroller CPU 100 controls a buzzer 132, which in the embodiment shown is a peizo buzzer, although other audible and/or visual indicators may be used, such as an external speaker or a light or LED. The microcontroller CPU 100 also controls a display 136, used to indicate several different pieces of information to the user. In one embodiment, the display is a 16×2 character liquid crystal display. In will be understood that a number of suitable displays could be used, including a flat panel display or a CRT type display.

The microcontroller CPU 100 also receives input from a real time clock 140. This input can be used to display the current time on the display 136, and/or to log the time of any respiratory measurements taken. The microcontroller CPU 100 also receives input from a keypad 144. This input is used for control functions for a user. It should be understood that other input devices may be used to input commands into the respiratory measurement device, including a device which may be present on the serial communications connector 128, such as another device or a keyboard which is connected to the serial communications connector 128.

The respiratory measurement device 20 also has a memory 148, which the microcontroller CPU 100 has access to for storing and retrieving stored data, which may include operating programs as well as previously stored data for different users. In one embodiment, the memory 148 includes a primary memory portion 152, and a secondary memory portion 156. The primary memory portion 152 is a non-volatile memory which can store user information, operating information, and any other required data. The secondary memory portion 156 includes calibration information regarding the calibration information for the flow tube 28, and can contain data indicating the number of measurements taken with the respiratory measurement device 20. In one embodiment, the memory element 36 described above with respect to FIGS. 1–4 contains the secondary memory portion 156. In this embodiment, the primary memory portion 152 is an EEPROM, and the secondary memory portion 156 is an EEPROM. The secondary memory portion 156 in this embodiment is physically an externally connected EEPROM, as described above, and is addressed as a part of the memory 148, thus the microcontroller CPU 100 accesses the primary and secondary memory portions 152, 156 as if they were a single physical memory. It will be understood that other data storage devices may be used as the memory 148, including magnetic media and optical media. These other data storage devices may be used as either, or both, the primary and secondary memory portions 152, 156.

Figure 7:
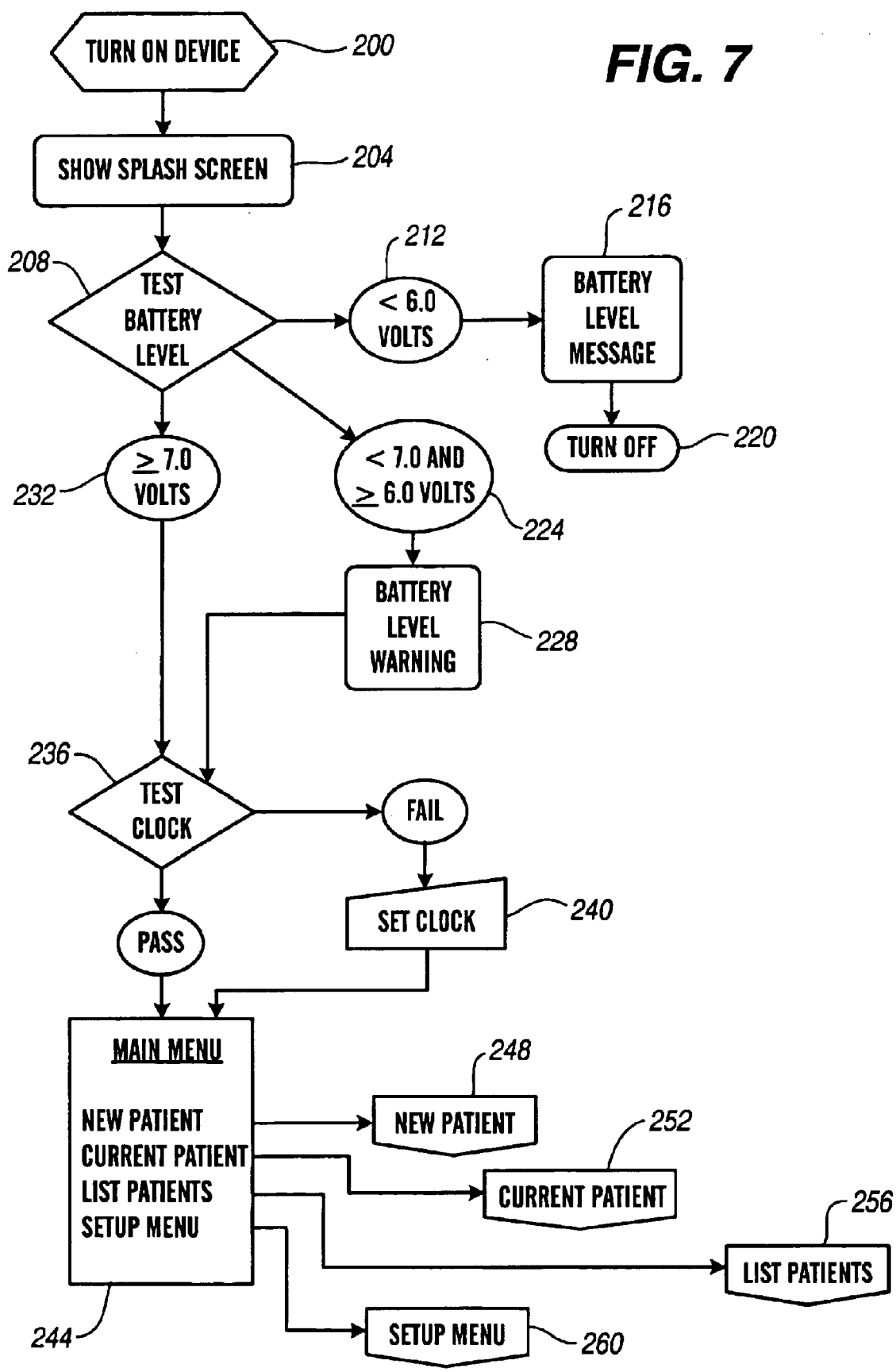
FIG. 7 is a flow chart illustrating the power on and initialization operation of one embodiment of the present invention.

Referring now to the flow chart illustration of FIG. 7, the operation of the respiratory measurement device 20 will now be described. Initially, as indicated at block 200, the respiratory measurement device is turned on. Upon being turned on, the device will display a splash screen on the display, as indicated at block 204. In one embodiment, the respiratory measurement device operates using a 9V battery as its power source. In this embodiment, the level of the battery is tested, according to block 208. If the battery level is less than 6 volts, the device displays a battery level message, and then powers off, as indicated at blocks 212, 216 and 220. If the battery level is 6V or greater, but less than 7V, the device then displays a battery level warning, as indicated at blocks 224 and 228. If the battery level is 7V or greater, the battery level test is passed, as indicated at block 232.

Following the battery test, the system then performs a clock test, as indicated at block 236. If the clock test fails, the system requests the user to set the clock, as indicated at block 240. Following the clock setting, if the clock test failed, or following a successful clock test, the system then displays the main menu, as indicated at block 244. The main menu in this embodiment has four options, new patient indicated at block 248, current patient indicated at block 252, list patients indicated at block 256, and setup menu indicated at block 260.

Figure 8:
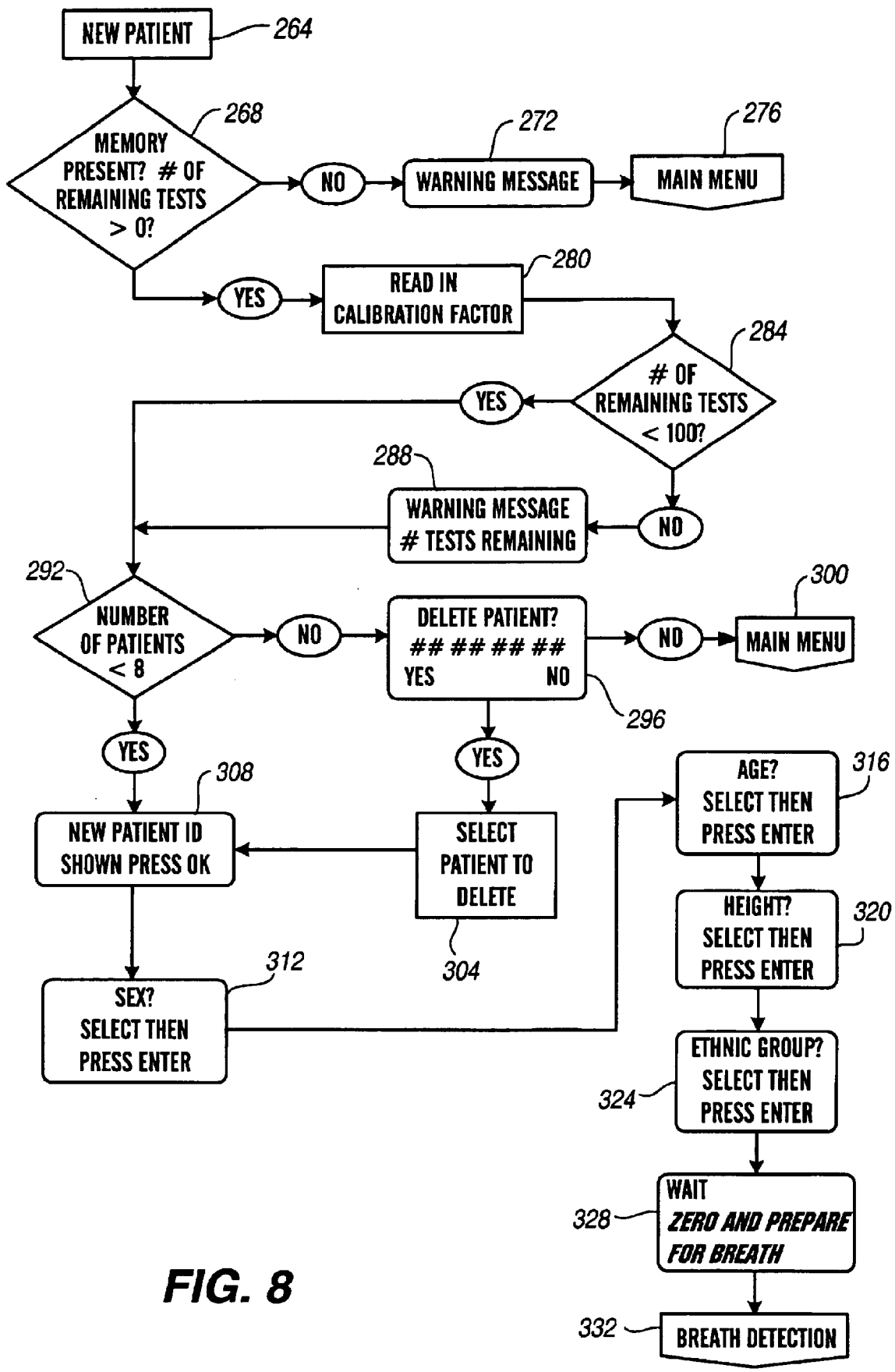
FIG. 8 is a flow chart illustrating the operation for taking a respiratory measurement for a new patient for a respiratory measurement device of one embodiment of the present invention.

Referring now to the flow chart of FIG. 8, the operation of the respiratory measurement device when a new patient is using the device is now described. Initially, according to block 264, the "New Patient" option is selected from the main menu. When the device receives this input, it determines whether a valid memory element is present, as indicated at block 268. Whether a valid memory element is present includes a determination of where there is a memory element present at all, and if so, whether there are any remaining tests which can be taken using the current memory element. In one embodiment, the number of tests which can be taken with a memory element corresponds to the number of flow tubes included in a lot or a batch. In another embodiment, each flow tube may be used a number of times, and the memory element includes information related to the number of measurements for a flow tube.

If the device determines that there is not a valid memory element, a warning message is displayed, according to block 272. The device then returns to the main menu, as indicated at block 276. If a valid memory element is present, the device reads information related to the calibration of the flow tube from the memory element, as indicated at block 280. Next, the device determines if the number of remaining tests is less than a predetermined number, which is this embodiment is 100, as indicated at block 284. If the number of remaining tests is less than the predetermined number, the device displays a warning message indicating the number of remaining tests, as indicated at block 288.

Next, according to block 292, the device determines whether the number of patients with data already stored on the device is fewer than the maximum number of patients that the device has memory to store, which in this embodiment is 8 patients. If the number of existing patients is the maximum number of patients, the device prompts the user, asking whether to delete a patient, as indicated at block 296. If the user inputs a negative response to deleting a patient, the device returns to the main menu, as indicated at block 300. If the user inputs that a patient is to be deleted, the user selects which of the current patients is to be deleted, as indicated at block 304.

Following the selection of the patient to delete from block 304, or when the existing number of patients was fewer than the maximum as determined at block 292, the device then generates a new patient identification, which is displayed to the user for approval, as indicated at block 308. Following the user approval of the new patient identification, a series of treatment related questions are asked. The first question is the sex of the patient, as indicated at block 312. Following the selection of the patient sex, the device prompts the user to select the age of the patient, as indicated at block 316. Following the selection of the patient age, as noted at block 320, the device prompts the user to enter the height of the patient. Once the height is selected, the device prompts the user for the ethnic group of the patient, as indicated at block 324. Following the selection of the ethnic group, the device resets the measurement components and prepares to receive a measurement, according to block 328. The device then shifts to breath detection, as indicated at block 332.

Figure 9:
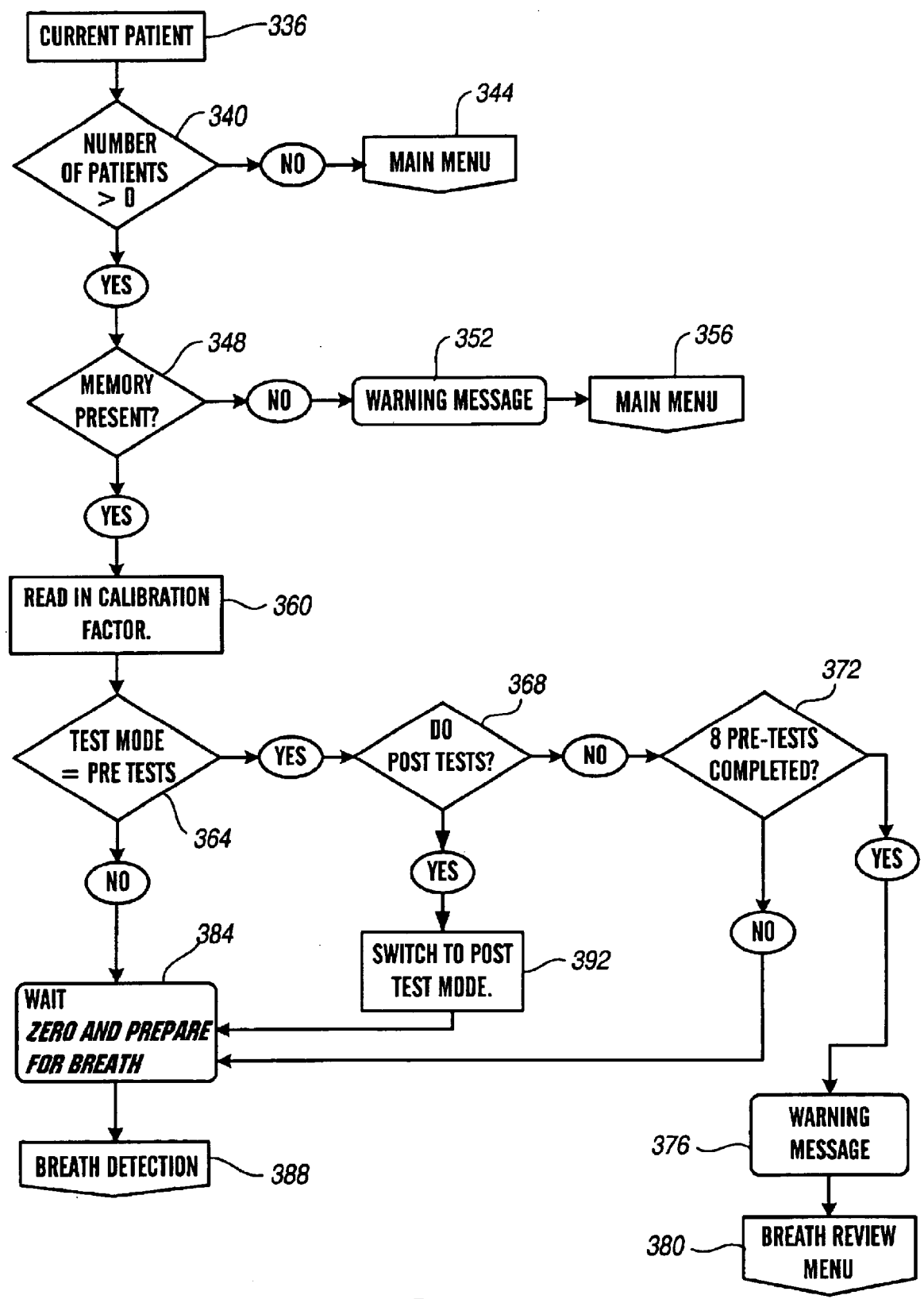
FIG. 9 is a flow chart illustrating the operation for taking a respiratory measurement for a current patient for a respiratory measurement device of one embodiment of the present invention.

With reference now to FIG. 9, the operation of the respiratory measurement device when the user selects a current patient from the main menu is now described. As discussed above with respect to FIG. 7, the user may select a current patient from the main menu. When current patient is selected, as indicated at block 336 of FIG. 9, the device then determines whether the current number of patients is greater than zero, as noted at block 340. If there are zero current patients which have associated data, the device returns to the main menu, as indicated at block 344. If the number of current patients is greater than zero, the device then determines whether a memory element is present, as indicated at block 348. If there is no memory element present, the device displays a warning message, as indicated at block 352. The device then returns to the main menu, as indicated at block 356.

If a memory element is present, the device then determines the calibration information which is stored in the memory element, as noted by block 360. The device then determines the testing mode that the user has selected, as indicated at block 364. In this embodiment, there are two testing modes, which are pre-test, and post test. Pre-test is used to establish a baseline for a patient. When conducting a post test, the test results of the pre-test can be compared with the results of the post test. If the device is in pre-test mode, the user is prompted on whether to conduct post tests, as indicated at block 368. If the user indicates that post tests are not to be performed, the device then determines whether 8 pre-tests have been completed, as indicated at block 372. If 8 pre-tests have been completed, the device displays a warning message indicating that the pre-tests have been completed, as indicated at block 376. The device then displays the breath review menu, as noted by block 380. If 8 pre-tests have not been completed, the device resets the measurement components and prepares to detect a breath, as indicated at block 384. The device then shifts to breath detection operation, as indicated at block 388. If at block 368 the user indicates that a post test is to be performed, the device switches to post test mode, as indicated at block 392. The device then resets the measurement components and prepares to detect a breath as indicated at block 384, and then switches to breath detection operation as indicated by block 388.

Figure 10:
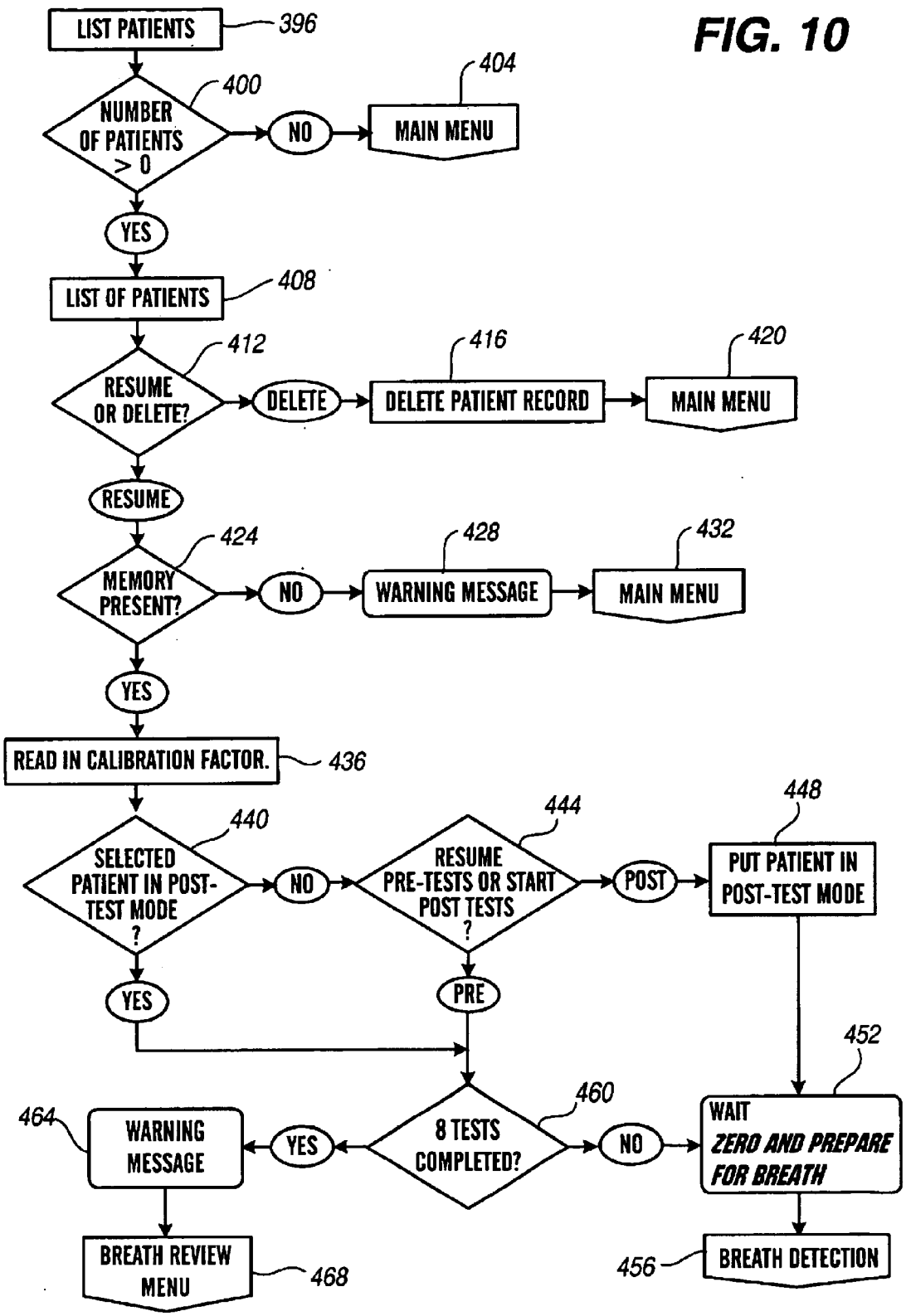
FIG. 10 is a flow chart illustrating the operation for listing patients stored in memory for a respiratory measurement device of one embodiment of the present invention.

Referring now to the flow chart illustration of FIG. 10, the operation of the device when the list patients option is selected from the main menu is now described. Initially, as noted by block 396, the user selects the "List Patients" option from the main menu. The device then, at block 400, determines if there are currently any patients which have associated data stored in memory. If there are no current patients, the device displays the main menu, as indicated at block 404. If there are any current patients, the device displays a listing of the current patients, as indicated by block 408. The device also prompts the user whether to resume or to delete a patient, as indicated by block 412. If the user selects the delete option, the device deletes the selected patient record, as indicated by block 416. The device then displays the main menu, as noted at block 420. If at block 412 the user selects the resume option, the device determines whether a memory element is present, as indicated by block 424. If no memory element is present, the device displays a warning message, as indicated by block 428. The device then displays the main menu, according to block 432. If the memory element is present, the device determines the calibration information which is present on the memory element, as noted by block 436.

The device next, at block 440, determines whether the selected patient is in post test mode. If the patient is not in post test mode, the user is prompted on whether to resume pre-tests or to start post tests, according to block 444. If the user selects post tests, the patient is switched to post test mode, according to block 448. The device then resets the measurement components and prepares for a breath, as noted by block 452. The device then shifts to breath detection operation, as indicated at block 456. If at block 444 the user selects the resumption of pre-tests, the device determines whether 8 pre-tests have been completed, as indicated by block 460. If fewer than 8 pre-tests have been completed, the device resets the measurement components and prepares for a breath, as noted by block 452. The device then shifts to breath detection operation as indicated by block 456.

If at block 440 the device determines that the selected patient is in post test mode, the device then determines whether 8 tests have been completed, as indicated at block 460. If 8 tests have been completed, the device displays a warning message, according to block 464. The device then displays the breath review menu, as noted by block 468. If 8 tests have not been completed, the device resets the measurement electronics and prepares for a breath, as indicated at block 452. The device then shifts to breath detection operation, as indicated by block 456.

Figure 11:
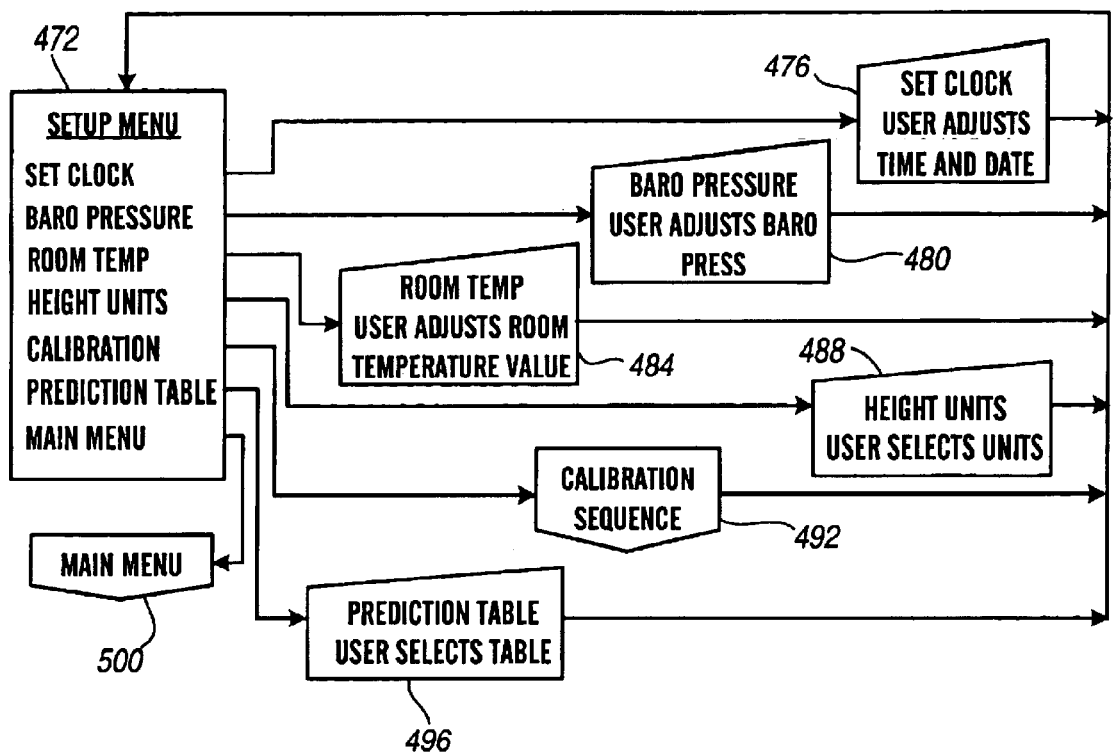
FIG. 11 is a flow chart illustrating the operation of the setup menu for a respiratory measurement device of one embodiment of the present invention.

Referring now to FIG. 11, the setup menu for the device is now described. As discussed above with respect to FIG. 7, one option from the main menu is a setup menu. The setup menu, as indicated by block 472 of FIG. 11, contains several options. The user may select a "Set Clock" option which, when selected, prompts the user to adjust the time and date, as noted by block 476. The user may also select a "Baro Pressure" option, after which the device prompts the user to adjust the barometric pressure, as noted by block 480. A "Room Temp" option is also available, and if selected, the device prompts the user to adjust a room temperature value, as indicated by block 484. The user may select a "Height Units" option, after which the device prompts the user to select the units that height is measured in, as indicated by block 488. A "Calibration" option is also available, which, if selected, initiates a calibration sequence, as indicated by block 492 and will be described in more detail below. The user may also select a "Prediction Table" option, after which the device displays a number of prediction table options and prompts the user to select a table, as indicated by block 496. The prediction tables are used for comparing measured test values to values expected for a person of the same physical characeristics with normal lungs. Finally, the user may select a "Main Menu" option, which will display the main menu, as noted by block 500. Following the completion of the functions described with respect to blocks 476, 480, 484, 488, 492, and 496, the device returns the display to the setup menu display.

Figure 12:
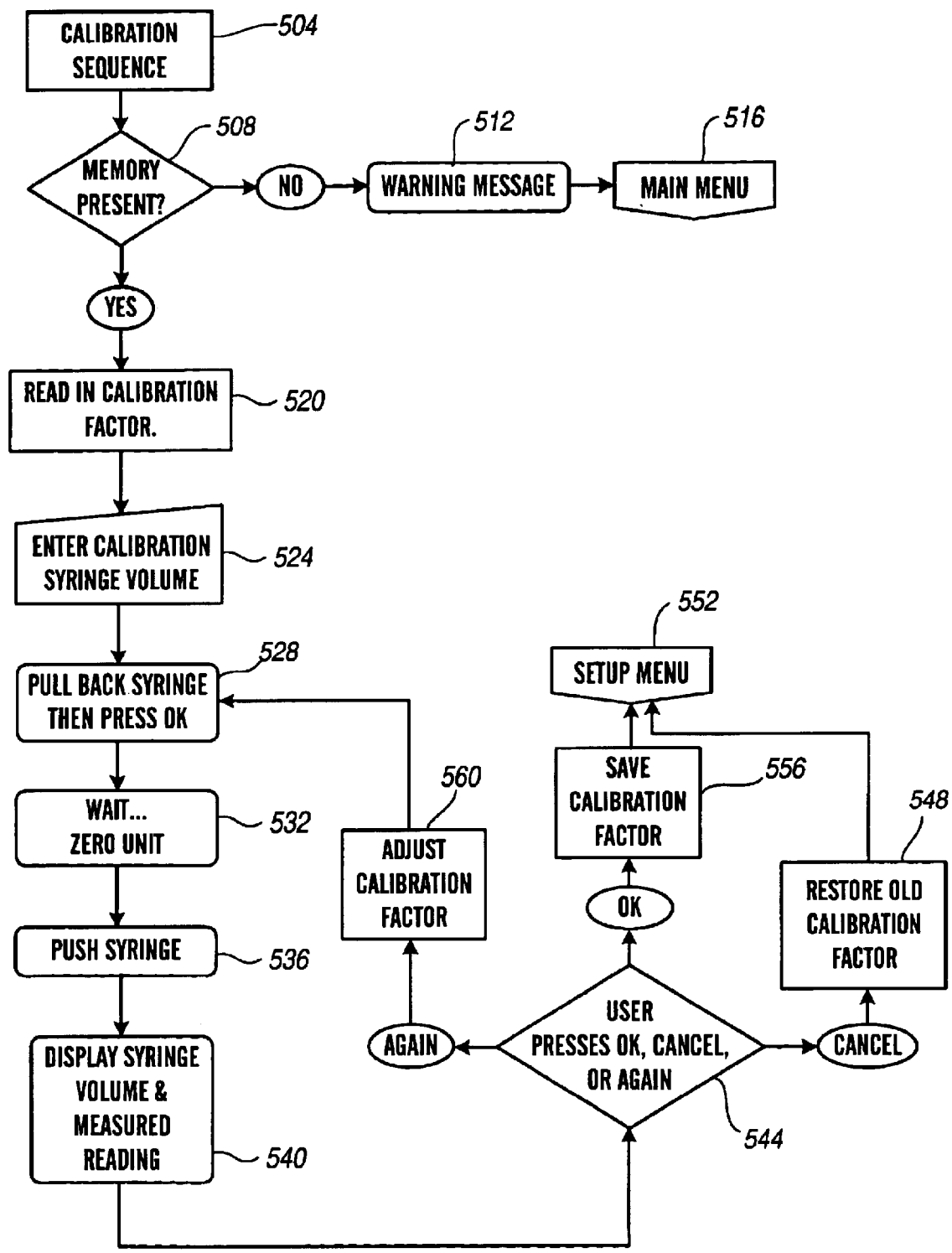
FIG. 12 is a flow chart illustrating the operation of the calibration sequence for a respiratory measurement device of one embodiment of the present invention.

Referring now to FIG. 12, the calibration sequence will now be described. As indicated by block 504, the calibration sequence is initiated by a user. The device then determines whether a memory element is present, according to block 508. If a memory element is not present, the device displays a warning message indicating that the memory element is not present, as noted by block 512. The device then returns the display to the main menu, as noted by block 516. If the memory element is present, the device determines the calibration information present in the memory element, as noted by block 520. The device next prompts the user to enter the volume of the calibration syringe, as indicated by block 524. Next, according to block 528, the device prompts the user to pull back the syringe, and then press a button to indicate that the syringe is pulled back. The device then resets the measurement components, according to block 532. The device next prompts the user to push the syringe, as indicated by block 536. The device then displays the syringe volume and measured reading, as noted by block 540. The device next prompts the user to press "OK," "Cancel," or "Again" as noted by block 544. If the user selects "Cancel," the device restores the old calibration factor, as noted by block 548. The device then returns to the setup menu, as indicated by block 552. If the user depresses "OK" in response to block 544, the device saves the calibration factor, as noted by block 556. The device then returns to the setup menu, noted by block 552. If the user depresses "Again" in response to block 544, the device enters an adjust calibration factor routine, as noted by block 560. The device then repeats the steps outlined above with respect to blocks 528 through 544.

Figure 13:
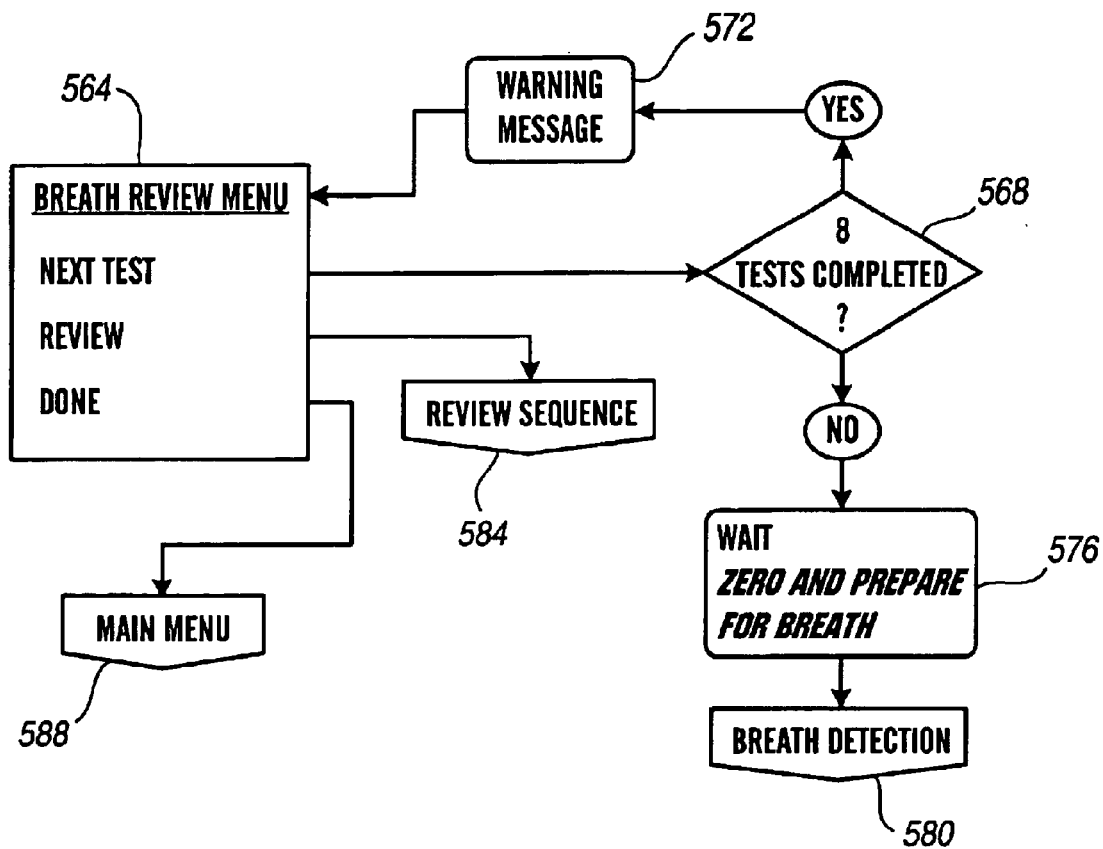
FIG. 13 is a flow chart illustrating the operation of the breath review menu for a respiratory measurement device of one embodiment of the present invention.

Referring now to FIG. 13, the breath review menu is now described. The breath menu in this embodiment, as indicated by block 564, includes three options, Next Test, Review, and Done. If the user selects the next test option, the device determines if 8 tests have been completed, as noted by block 568. If eight tests have been completed, the device displays a warning message indicating that eight tests are completed, as indicated by block 572. The breath review menu is then displayed, as noted by block 564. If eight tests have not been completed, the device resets the measurement components, and prepares for a breath, as indicated by block 576. The device then shifts to breath detection mode, as noted by block 580. If the user selects the review option from the breath review menu, the device switches to the review sequence, as noted by block 584 and will be described in more detail below. If the user selects the done option, the device shifts back to the main menu, according to block 588.

Figure 14:
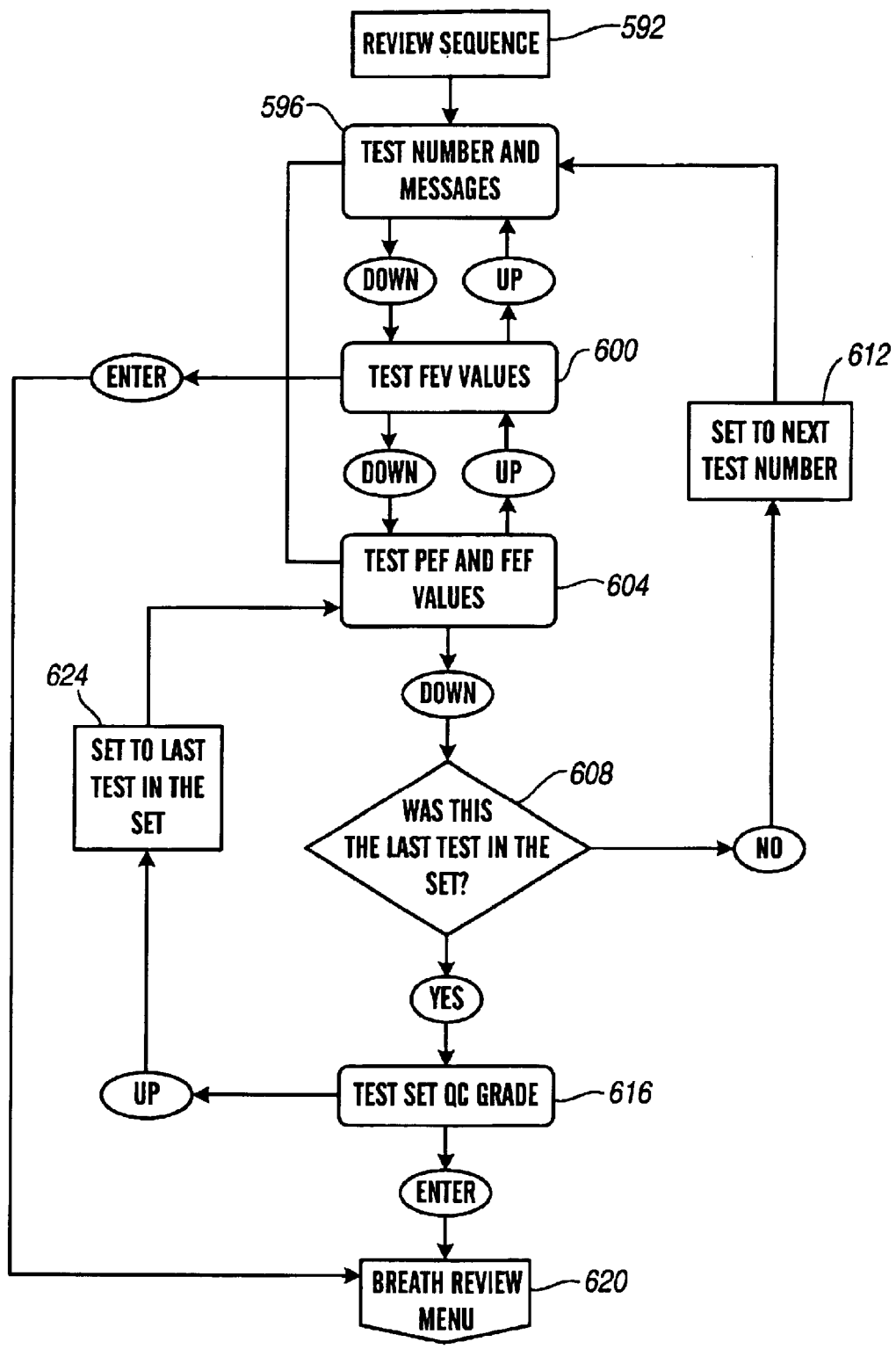
FIG. 14 is a flow chart illustrating the operation of the measurement result review sequence for a respiratory measurement device of one embodiment of the present invention.

With reference now to FIG. 14, the review sequence is now described. According to block 592, the user selects the review sequence. The device next displays the test number and massages, as indicated at block 596. The user can then select a test number, and depress a key associated with a down arrow, taking the user to a display of test FEV values, as indicated at block 600. The user can then depress a key associated with a down arrow, taking the user to a display of test PEF and FEF values, as indicated by block 604. The user may then depress a key associated with a down arrow, at which point the device will determine if the information displayed was for the last test in the test set, as indicated at block 608. If the information was not for the last test in the test set, the device displays the test number and messages, as noted by block 612. If the information was for the last test in the test set, the device displays a test set QC grade, as noted by block 616. The user can then depress the enter key, returning the display to the breath review menu, as indicated by block 620. The user can also depress a key associated with an up arrow, at which point the device will set the test number to the last test in the test set, as noted by block 624, and return the user to the display associated with block 604. At any point when the device is displaying the information associated with blocks 600, and 604, the user may also depress a key associated with an up arrow. If the user depresses the up arrow button while viewing the test PEF and FEF values associated with block 604, the device will display the test FEV values associated with block 600. If the user depresses the up arrow button while viewing the test FEV values, the device will display the test number and messages associated with block 596. Furthermore, at any point while viewing the information associated with blocks 596, 600, and 604, the user may depress the enter key, which will result in the device displaying the breath review menu, as noted by block 620.

Figure 15:
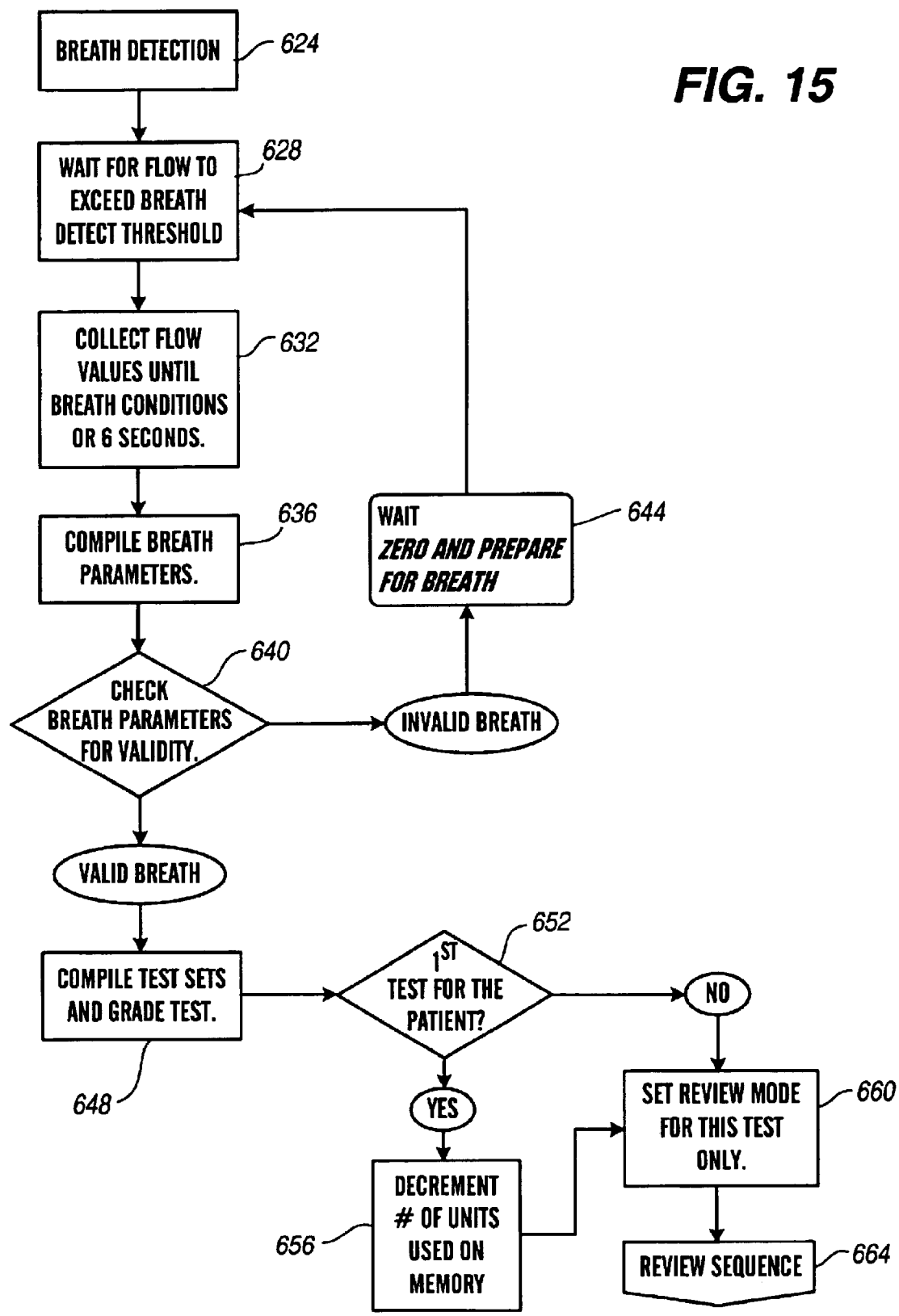
FIG. 15 is a flow chart illustrating the operation for taking a respiratory measurement for a respiratory measurement device of one embodiment of the present invention.

Referring now to FIG. 15, a flow chart illustration of a breath detection operation is now described. Initially, the device is shifted to breath detection mode, as noted by block 624. The device then waits for measured air flow to exceed a breath detect threshold, as noted by block 628. The breath detect threshold is a minimum pressure which must be read at the pressure sensing transducer, which in one embodiment is the pressure necessary to equate to 5 liters per minute. The device then collects flow values until breath conditions or for six seconds, as indicated by block 632. Next, according to block 636, the device compiles the breath parameters. The device then determines if the compiled breath parameters are valid, as noted by block 640. If the breath was not valid, the device resets the measurement components, and prepares for a breath, as indicated by block 644. The device then repeats the steps described with respect to blocks 628 through 640. If the breath was valid, the device compiles the test sets and grades the test, as noted by block 648. The device then determines whether this was the first test for the patient, as indicated by block 652. If this was the first test for the patient, the device decrements the number of valid tests remaining for the memory element, as noted by block 656. The device then displays the breath review menu for this test only, as noted by block 660. Next, the device goes to the review sequence, as noted by block 664. If this was not the first test for the patient, the device completes the steps described with respect to blocks 660 and 664.

While the operation of the respiratory measurement device as described with respect to the flow charts of FIGS. 7 through 15 describe a device which decrements a counter contained within a memory element, alternative embodiments for using a counter to track usage of a respiratory measurement device are readily available, and within the scope of the present disclosure. For example, in one alternative embodiment, the memory element contains a usage number in memory which is incremented, rather than decremented, when a new test is performed. In this embodiment, the respiratory measurement device contains a predetermined number of tests, and reads the usage number from the memory element, and compares that number with the predetermined number to determine whether any additional measurements may be taken with that memory element, or whether to display a warning indicating the number of remaining tests. In this embodiment, the predetermined number which is stored in the primary memory along corresponds to the number of flow tubes contained in a lot or batch of flow tubes.

In another alternative embodiment, the memory element is contained on the flow tube itself (or on a detachable element that is separate from the flow tube), and contains a usage flag. In one configuration, a disposable flow tube is engaged with the body member of the respiratory measurement device. The device determines the state of the usage flag. If the usage flag is set (or not set), it indicates that the flow tube (or associated lot of flow tubes) has been used, and the respiratory measurement device does not allow that flow tube (or lot of flow tubes) to be used for a respiratory measurement. If the usage flag is not set (or set), the respiratory measurement device reads calibration information from the memory element, and allows the predetermined number of respiratory measurements to be performed (by reinitializing the counter). At the completion of the predetermined number of respiratory measurements, the device sets (or unsets) the usage flag, indicating that the flow tube has been used. To track the specific flow tube, a flow tube identifier (that is unique to a flow tube or lot of flow tubes) can be in the memory element to permit the device to track the number of tests performed by that flow tube (or lot of flow tubes). In this way, removal of the flow tube before the flag is set (or not set) can be accounted for. In one configuration, a lot size value is also in the memory element to permit the counter to be reinitialized to the proper value (depending on the lot size value). The lot size value is typically related to the number of flow tubes in the corresponding lot.

In another embodiment, the memory element contains information indicating the lot number of the lot of flow tubes to which it is associated. This lot number is displayed on the display of the respiratory measurement device, and can be compared to a lot number which is printed on the flow tubes, or on a container which houses a number of flow tubes which are associated with the memory element.

In another embodiment, the flow tubes are binned depending upon physical characteristics of the flow tube, in a similar manner as described above. Each of the bins has an associated color, or number. The number or color is affixed to the flow tubes in that bin, and the memory element associated with a lot of flow tubes contains information related to the color or number. The respiratory measurement device reads the number or color information, and displays the number or color. A user then compares the displayed color or number to the color or number affixed to the flow tube which is to be used for the respiratory measurement. If the number of color are the same, the calibration information is correct, and if the number or color are different, the calibration information stored on the memory element for the flow tube is not correct. The user may then correct either the memory element, or the flow tube. The respiratory measurement device in one embodiment further includes a prompt for the user to enter the color or number which appears on the flow tube, and compares this with the color or number information contained in the memory element to verify that the proper calibration factor is used in the respiratory measurement.

The embodiments described herein above are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A respiratory device for measuring a pulmonary condition of a patient, comprising:

a processor in a respiratory measurement device operable to determine at least a first respiratory parameter based on at least a first measurement signal;

a monitoring unit comprising a memory operable to store calibration information to determine the at least a first respiratory parameter and a counter for tracking a number of respiratory measurements performed by the respiratory device; and at least a first detachable component operable to receive a respiratory airflow of a user, wherein the monitoring unit is not part of the first detachable component and detachably engages the respiratory measurement device.

2. The respiratory device of claim 1, wherein the at least a first detachable component provides the at least a first measurement signal.

3. The respiratory device of claim 1, wherein the memory is operable to store a flag for determining if the at least a first detachable component has been used in taking a predetermined number of respiratory measurements.

4. The respiratory device of claim 1, wherein the processor and memory are contained in a body member, the at least a first detachable component is detachable from the body member, the at least a first detachable component is disposable, and the body member is reusable.

5. The respiratory device of claim 1, wherein the at least a first respiratory parameter is one or more of PEF, FEV1, FEV6, FEV1/FEV6, FVC, FEV1/FVC, and FEF25–75 and wherein the respiratory measurement is enabled when a current value of the counter is less than a selected number of respiratory measurements and disabled when the current value of the counter is equal to the selected number of respiratory measurements.

6. The respiratory device of claim 1, wherein the processor is contained in a body member, and wherein the monitoring unit is separate from the respiratory measurement device.

7. The respiratory device of claim 1, wherein the memory is one or more of ROM, PROM, EPROM, flash memory, non-volatile RAM, battery-backed-up RAM, EEPROM, a magnetic disk, and an optical disk and further comprising a second memory in the respiratory measurement device.

8. A monitoring device for detachable engagement with at least a portion of a respiratory measurement device, comprising:
   a memory including calibration information for measurements of the respiratory device;
   a counter that determines a number of measurements taken by the respiratory measurement device; and
   a state indicator, wherein, when a current value of the counter is different from a selected number of measurements, the state indicator indicates that the respiratory measurement device is enabled and, when the current counter value is the same as the selected number of measurements, the state indicator indicates that the respiratory measurement device is disabled.

9. The monitoring device of claim 8, further comprising a flow tube, and a body member that removably engages the flow tube and wherein the state indicator is a usage flag.

10. The monitoring device of claim 9, wherein the flow tube is disposable and the body member is reusable.

11. The monitoring device of claim 9, wherein the measurements determine a respiratory parameter that is one or more of PEF, FEV1, FEV6, FEV1/FEV6, FVC, FEV1/FVC, and FEF25–75 and wherein the monitoring device is not part of the flow tube.

12. The monitoring device of claim 9, wherein the monitoring device is detachable from the respiratory measurement device and a processor is contained in the respiratory measurement device.

13. The monitoring device of claim 8, wherein the memory is one or more of ROM, PROM, EPROM, flash memory, non-volatile RAM, battery-backed-up RAM, EEPROM, a magnetic disk, and an optical disk and wherein the respiratory measurement device comprises memory different from the memory of the monitoring device.

14. A method for monitoring use of a respiratory measurement device, comprising:
   (a) engaging a flow tube with at least a portion of the respiratory measurement device;
   (b) engaging a monitoring unit with the at least a portion of the respiratory measurement device, the monitoring unit including a memory including calibration information associated with at least one of the respiratory measurement device and the flow tube and a counter for determining a number of measurements taken by the respiratory measurement device;
   (c) performing a respiratory measurement with the respiratory measurement device; and
   (d) at least one of decrementing and incrementing the counter in response to the performing step, wherein the monitoring unit is not part of the flow tube and detachably engages the respiratory measurement device.

15. The method of claim 14, further comprising, after step (d),
   (e) removing the flow tube from the respiratory measurement device; and
   (f) engaging a second flow tube with the respiratory measurement device.

16. The method of claim 15, further comprising, after step (f), repeating steps (c) and (d).

17. The method of claim 14, further comprising, after step (d),
   (e) comparing the counter value with a predetermined value;
   (f) when the counter value is the same as the predetermined value, disabling the respiratory measurement device; and
   (g) when the counter value is different from the predetermined value, enabling the respiratory measurement device.

18. The method of claim 17, wherein the predetermined value is zero.

19. The method of claim 17, further comprising, when step (f) occurs,
   (h) removing the monitoring unit from the respiratory measurement device;
   (i) engaging a second monitoring unit with the respiratory measurement device; and
   (j) enabling the respiratory measurement device in response to step (i).

20. The method of claim 19, wherein step (j) includes the steps of reading both a second memory and a second counter in the second monitoring unit.

21. A method for monitoring use of a respiratory measurement device, comprising:
   (a) providing a monitoring unit in detachable engagement with at least a portion of the respiratory measurement device, the monitoring unit including a memory;
   (b) performing a respiratory measurement with the respiratory measurement device;
   (c) at least one of decrementing and incrementing a counter in response to the performing step to provide a counter value;
   (d) comparing the counter value with a predetermined value;
   (e) enabling the respiratory measurement device when the counter value is different from the predetermined value; and
   (f) disabling the respiratory measurement device when the counter value is the same as the predetermined value.

22. The method of claim 21, wherein step (b) includes engaging at least part of a flow tube with the respiratory measurement device, and performing a respiratory measurement with the respiratory measurement device.

23. The method of claim 22, further comprising after step (c),
  (d) removing the flow tube from the respiratory measurement device; and
  (e) engaging a second flow tube with the respiratory measurement device.

24. The method of claim 23, further comprising after step (e), repeating steps (b) and (c).

25. The method of claim 22, wherein said memory contains information associated with the flow tube.

26. The method of claim 25, wherein the information includes calibration information for the flow tube and usage information for determining a number of measurements taken by the respiratory measurement device.

27. The method of claim 26, wherein the counter value indicates the number of measurements taken by the respiratory measurement device.

28. The method of claim 21, wherein the predetermined value is zero.

29. The method of claim 21, wherein the monitoring unit is detachable from the respiratory measurement device and further comprising, when step (f) occurs,
  (g) removing the monitoring unit from the respiratory measurement device;
  (h) engaging a second monitoring unit with the respiratory measurement device; and
  (i) enabling the respiratory measurement device in response to step (h).

30. A monitoring device for detachable engagement with a respiratory device, comprising:
  memory means including counting means for counting a number of measurements taken by the respiratory device, and state indicating means for indicating, when the memory means is engaged with the respiratory device and the number of measurements taken by the respiratory device is different from a selected number, that the respiratory device is enabled and, when the memory means is engaged with the respiratory device and the number of measurements taken by the respiratory device is equal to the selected number, that the respiratory device is disabled.

31. The monitoring device of claim 30, wherein the memory means also include calibration information associated with a measurement signal generated by sensing means for sensing a respiratory parameter.

32. The monitoring device of claim 30, further comprising:
  measuring means for measuring a respiratory parameter, wherein the measuring means is at least one of a flow tube, a pneumotach, a respiratory filter and a mouthpiece and wherein the state indicating means is a usage flag.

33. The monitoring device of claim 32, further comprising:
  processing means for processing a measurement signal output by the measuring means, the processing means being detachable from the measuring means.

34. The monitoring device of claim 33, wherein the memory means is detachable from the processing means.

35. The monitoring device of claim 33, wherein the respiratory parameter is at least one of PEF, FEV1, FEV6, FEV1/FEV6, FVC, FEV1/FVC, and FEF25–75 and wherein the monitoring device is not part of a flow tube engaged with the respiratory device.

36. A monitoring device for detachable engagement with a respiratory device, comprising:
  memory for storing a number of measurements taken by the respiratory device; and
  a processor operable, when the memory is engaged with the respiratory device and the number of measurements taken by the respiratory device is different from a selected number, to enable the respiratory device and, when the memory is engaged with the respiratory device and the number of measurements taken by the respiratory device is equal to the selected number, to disable the respiratory device.

37. The monitoring device of claim 36, wherein said memory also includes calibration information associated with a measurement signal generated by a sensor operable to sense a respiratory parameter and the respiratory device comprises memory different from the memory of the monitoring device.

38. The monitoring device of claim 36, further comprising:
  a measurement unit operable to measure a respiratory parameter, wherein the measurement unit is at least one of a flow tube, a pneumotach, a respiratory filter and a mouthpiece and wherein the monitoring device is not part of the measurement unit.

39. The monitoring device of claim 37, wherein the processor is operable to process a measurement signal output by the measurement unit, the processor being detachable from the measurement unit.

40. The monitoring device of claim 39, wherein the memory is detachable from the processor.

41. The monitoring device of claim 40, wherein the respiratory parameter is at least one of PEF, FEV1, FEV6, FEV1/FEV6, FVC, FEV1/FVC, and FEF25–75 and wherein the memory comprises a counter for deriving the number of measurements.

42. A method for supplying a disposable component for a respiratory measurement device, comprising:
  (a) manufacturing at least a first disposable component for a respiratory measurement device;
  (b) providing first calibration information for the first disposable component;
  (c) manufacturing a first enabling device, including a first memory storing at least one of the first calibration information and a first counter for counting a number of measurements performed by the respiratory measurement device; and
  (d) packaging at least the first disposable component together with the corresponding first enabling device for use by a respiratory measurement device user;
  (e) manufacturing at least a second disposable component;
  (f) determining second calibration information for the second disposable component;
  (g) manufacturing a second enabling device, including a second memory storing at least one of the second calibration information and a second counter for counting a number of measurements performed by a respiratory measurement device attached to at least the second disposable component; and
  (h) packaging at least the second disposable component together with the corresponding second enabling device for use by a respiratory measurement device user, wherein the second disposable component and second enabling device are in a different package than the first disposable component and first enabling device.

43. The manufacturing method of claim 42, wherein step (a) includes manufacturing a first plurality of disposable components, and wherein step (b) includes determining first calibration information for the first plurality of disposable components.

44. The manufacturing method of claim 42, wherein step (a) includes manufacturing a first plurality of disposable components, wherein step (b) includes determining first calibration information for the first plurality of disposable components, wherein step (e) includes manufacturing a second plurality of disposable components, and wherein step (f) includes determining second calibration information for the second plurality of disposable components.

45. The manufacturing method of claim 43, wherein the disposable components are at least one of a flow tube, a pneumotach, a respiratory filter and a mouthpiece.

46. The manufacturing method of claim 42, wherein the first calibration information differs from the second calibration information.

47. The manufacturing method of claim 42, wherein the first counter has the same value as the second counter.

48. A method for monitoring use of a respiratory measurement device, comprising:
(a) engaging a flow tube with the respiratory measurement device;
(b) engaging a monitoring unit with the respiratory measurement device, the monitoring unit including a memory including calibration information associated with at least one of the respiratory measurement device and the flow tube and a counter for determining a number of measurements taken by the respiratory measurement device;
(c) performing a respiratory measurement with the respiratory measurement device; and
(d) at least one of decrementing and incrementing the counter in response to the performing step;
(e) comparing the counter value with a predetermined value;
(f) when the counter value is the same as the predetermined value, disabling the respiratory measurement device; and
(g) when the counter value is different from the predetermined value, enabling the respiratory measurement device.

49. The method of claim 49, wherein the predetermined value is zero.

50. The method of claim 48, further comprising, when step (f) occurs,
(h) removing the monitoring unit from the respiratory measurement device;
(i) engaging a second monitoring unit with the respiratory measurement device; and
(j) enabling the respiratory measurement device in response to step (i).

51. The method of claim 50, wherein step (j) includes the steps of reading both a second memory and a second counter in the second monitoring unit.

52. A method for supplying a disposable component for a respiratory measurement device, comprising:
(a) manufacturing at least a first disposable component for a respiratory measurement device;
(b) determining first calibration information for the first disposable component;
(c) manufacturing a first enabling device, including a first memory storing at least one of the first calibration information and a first counter for counting a number of measurements performed by the respiratory measurement device;
(d) packaging at least the first disposable component together with the corresponding first enabling device for use by a respiratory measurement device user;
(e) manufacturing at least a second disposable component;
(f) determining second calibration information for the second disposable component;
(g) manufacturing a second enabling device, including a second memory storing the second calibration information and a second counter for counting a number of measurements performed by a respiratory measurement device attached to at least the second disposable component; and
(h) packaging at least the second disposable component together with the corresponding second enabling device for use by a respiratory measurement device user wherein the first counter has the same value as the second counter.

53. The manufacturing method of claim 52, wherein step (a) includes manufacturing a first plurality of disposable components, and wherein step (b) includes determining first calibration information for the first plurality of disposable components.

54. The manufacturing method of claim 52, wherein the first memory stores the first calibration information and the second memory stores the second calibration information.

55. The manufacturing method of claim 52, wherein the first memory stores the first counter and the second memory stores the second counter.

56. A method for monitoring use of a respiratory measurement device, comprising:
(a) engaging a flow tube from a set of flow tubes with the respiratory measurement device;
(b) engaging a monitoring unit with a body member of the respiratory measurement device, the monitoring unit including a memory comprising usage information associated with the set of flow tubes;
(c) performing a respiratory measurement with the respiratory measurement device; and
(d) at least one of decrementing and incrementing a use counter in response to the performing step;
(e) comparing the use counter with a predetermined number of respiratory measurements;
(f) when the use counter is different from the predetermined number of respiratory measurements, enabling the respiratory measurement device; and
(g) when the use counter is the same as the predetermined number of respiratory measurements, disabling the respiratory measurement device.

57. The method of claim 56, wherein the usage information comprises the use counter.

58. The method of claim 56, wherein the usage information comprises a usage flag, the usage flag indicating in a first state that the set of flow tubes has been used the predetermined number of respiratory measurements and in a second state that the set of flow tubes has not been used the predetermined number of respiratory measurements.

59. The method of claim 56, wherein the usage information comprises a unique identifier associated with the set of flow tubes.

60. The method of claim 56, wherein the usage information comprises the number of flow tubes in the set of flow tubes.

61. The method of claim 56, wherein the monitoring unit is discrete from the set of flow tubes and the body member of the respiratory measurement device, wherein the monitoring unit detachably engages the respiratory measurement device, and wherein the body member comprises a memory different from the memory in the monitoring unit.

62. The method of claim 56, wherein the monitoring unit comprises calibration information associated with the set of flow tubes.

63. A respiratory measurement device, comprising:
(a) a detachable flow tube;
(b) a body member engaging the detachable flow tube;
(c) a processor; and
(d) a detachable monitoring unit engaging the body member, the monitoring unit including a memory comprising usage information associated with the detachable flow tube, wherein the processor is operable to (i) at least one of decrement and increment a use counter when a respiratory measurement is performed; (ii) compare the use counter with a predetermined number of respiratory measurements; (iii) when the use counter is different from the predetermined number of respiratory measurements, enable the respiratory measurement device; and (iv) when the use counter is the same as the predetermined number of respiratory measurements, disable the respiratory measurement device.

64. The device of claim 63, wherein the usage information comprises the use counter.

65. The device of claim 63, wherein the usage information comprises a usage flag, the usage flag indicating in a first state that the detachable flow tube has been used the predetermined number of respiratory measurements and in a second state that the detachable flow tube has not been used the predetermined number of respiratory measurements.

66. The device of claim 63, wherein the flow tube is a member of a set of flow tubes and the usage information is a unique identifier associated with the set of flow tubes.

67. The device of claim 63, wherein the flow tube is a member of a set of flow tubes and the usage information comprises the number of flow tubes in the set of flow tubes.

68. The device of claim 63, wherein the monitoring unit is discrete from the flow tube and the body member, wherein the processor is in the body member, end wherein the body member comprises a memory different from the memory in the monitoring unit.

69. The device of claim 63, wherein the monitoring unit comprises calibration information associated with the flow tube.

* * * * *